US012797012B2

(12) United States Patent
Landman et al.

(10) Patent No.: US 12,797,012 B2
(45) Date of Patent: Nov. 17, 2026

(54) CLASSIFICATION OF PAUSE-TRIGGERED EPISODES

(71) Applicant: Medtronic, Inc., Minneapolis, MN (US)

(72) Inventors: Sean R. Landman, Minneapolis, MN (US); Gautham Rajagopal, Minneapolis, MN (US)

(73) Assignee: Medtronic, Inc., Minneapolis, MN (US)

(*) Notice: Subject to any disclaimer, the term of this patent is extended or adjusted under 35 U.S.C. 154(b) by 981 days.

(21) Appl. No.: 16/864,871

(22) Filed: May 1, 2020

(65) Prior Publication Data

US 2021/0338168 A1 Nov. 4, 2021

(51) Int. Cl.

| | |
|---|---|
| ***A61N 1/05*** | (2006.01) |
| ***A61B 5/00*** | (2006.01) |
| ***A61B 5/287*** | (2021.01) |
| ***A61B 5/364*** | (2021.01) |
| ***G16H 50/30*** | (2018.01) |

(Continued)

(52) U.S. Cl.

CPC .......... *A61B 5/7221* (2013.01); *A61B 5/0006* (2013.01); *A61B 5/287* (2021.01); *A61B 5/364* (2021.01); *A61B 5/7203* (2013.01); *G16H 50/30* (2018.01); *A61N 1/3704* (2013.01); *A61N 1/3925* (2013.01); *A61N 1/3956* (2013.01)

(58) Field of Classification Search

CPC ........ A61B 5/363; A61B 5/349; A61N 1/3721

See application file for complete search history.

(56) References Cited

U.S. PATENT DOCUMENTS

| | | | |
|---|---|---|---|
| 6,304,773 | B1 | 10/2001 | Taylor et al. |
| 10,413,207 | B2 | 9/2019 | Sarkar et al. |
| 2011/0270107 | A1 | 11/2011 | Zhang et al. |

(Continued)

FOREIGN PATENT DOCUMENTS

| | | | |
|---|---|---|---|
| CN | 108882861 | A | 11/2018 |
| CN | 109688916 | A | 4/2019 |

OTHER PUBLICATIONS

Baudoin et al., "The Superior Epigastric Artery Does not Pass Through Larrey's Space (Trigonum Sternocostale)," Surg Radiol Anat, vol. 25, Aug. 1, 2003, 4 pp.

(Continued)

*Primary Examiner* — Michael J D'Abreu

(74) *Attorney, Agent, or Firm* — Shumaker & Sieffert, P.A.

(57) ABSTRACT

This disclosure is directed to techniques for identifying false detection of pause-triggered episode in cardiac ECG data. In some examples, a medical system is configured to receive a cardiac electrogram of a pause-triggered episode, the cardiac electrogram sensed by a medical device via a plurality of electrodes, determine whether one or more of false pause detection criteria are satisfied based on the cardiac electrogram, wherein the one or more of false pause detection criteria comprise: at least one criterion for relative flatness of amplitude values of the cardiac electrogram in a time interval between a last pre-pause beat and a pause detection time, classify the pause-triggered episode as one of a plurality of classifications based on the determination of whether the false pause detection criterion is satisfied, and output an indication of the classification of the pause-triggered episode to a user display.

19 Claims, 12 Drawing Sheets

(51) Int. Cl.

| | |
|---|---|
| *A61N 1/37* | (2006.01) |
| *A61N 1/39* | (2006.01) |

(56) References Cited

U.S. PATENT DOCUMENTS

| | | | | |
|---|---|---|---|---|
| 2012/0029373 | A1 | 2/2012 | Stadler et al. | |
| 2017/0273589 | A1 | 9/2017 | Sarkar et al. | |
| 2018/0064360 | A1* | 3/2018 | Siejko | A61B 5/364 |
| 2019/0192870 | A1 | 6/2019 | Zaidi et al. | |
| 2019/0343415 | A1* | 11/2019 | Saha | A61B 5/7282 |

OTHER PUBLICATIONS

International Search Report and Written Opinion of International Application No. PCT/US2021/028747, mailed Aug. 5, 2021, 16 pp.

Office Action from counterpart Chinese Application No. 202180032228.7 dated May 15, 2025, and translation thereof, 16 pp.

* cited by examiner

200

220

CLASSIFICATION OF PAUSE-TRIGGERED EPISODES

FIELD

The disclosure relates generally to medical systems and, more particularly, medical systems configured to detect cardiac pause episodes based on a cardiac electrogram.

BACKGROUND

Some types of medical devices may monitor a cardiac electrogram (EGM) of a patient to monitor the electrical activity of the patient's heart. A cardiac EGM is an electrical signal sensed via electrodes. In some examples, the medical devices monitor a cardiac EGM to detect one or more types of arrhythmia, such as bradycardia, tachycardia, fibrillation, or asystole, e.g., caused by sinus pause or AV block, which is referred to herein as cardiac pause.

SUMMARY

A cardiac EGM may include noise, artifacts, etc. in addition to the signal representing the electrical activity of the heart. Additionally, the amplitude of the signal representing the electrical activity of the heart within the cardiac EGM may vary over time, e.g., due to movement of the electrodes relative to the cardiac tissue. Noise, artifacts, and signal amplitude variations may confound detection of cardiac depolarizations and, consequently, the accurate identification of cardiac pause episodes using the cardiac EGM. This is partially due to the fact that when some cardiac depolarizations are undetected, one or more heartbeats are not accounted for in the cardiac EGM.

In general, the disclosure is directed to techniques for verifying detection of pause-triggered episodes in a cardiac EGM. The techniques include analyzing at least a portion of cardiac EGM data stored as a pause-triggered episode to determine whether the pause-triggered episode is most likely to be classified as a true pause (classification) or a false pause (classification) based upon one or more false pause detection criterion. In some examples, processing circuitry of a medical device/system performs this analysis in response to a pause-triggered episode detection criterion being satisfied.

In some examples, the processing circuitry of the medical device/system classifies the pause-triggered episode into one of a plurality of classifications based on the analysis, which may assist in prioritizing episodes for an episode review process by a qualified medical clinician. For example, if the processing circuitry determines that the pause-triggered episode is more likely a true pause, the processing circuitry may classify the pause-triggered episode as high priority episode in the review process, and if the processing circuitry determines that the pause-triggered episode is more likely a false pause episode, the processing circuitry may classify the pause-triggered episode either as normal priority episode or a low priority episode in the review process. The processing circuitry may utilize one or more false pause-triggered episode detection criterion to determine whether the pause-triggered episode is a likely false pause and to classify as the low priority episode or the normal low priority episode. At least one example criterion evaluates amplitude values to determine a relative flatness of the episode. In this manner, the techniques of this disclosure may advantageously enable improved accuracy in the identification of true pause, improved efficiency of review of pause episodes, and, consequently, better evaluation of the condition of the patient.

In one example, a medical system comprising processing circuitry and a storage medium, the processing circuitry configured to receive a cardiac electrogram of a pause-triggered episode, the cardiac electrogram sensed by a medical device via a plurality of electrodes, determine whether one or more of false pause detection criteria are satisfied based on the cardiac electrogram, wherein the one or more of false pause detection criteria comprise: at least one criterion for relative flatness of amplitude values of the cardiac electrogram in a time interval between a last pre-pause beat and a pause detection time, classify the pause-triggered episode as one of a plurality of classifications based on the determination of whether the false pause detection criterion is satisfied, and output an indication of the classification of the pause-triggered episode to a user display.

In another example, a method comprises receiving a cardiac electrogram of a pause-triggered episode, the cardiac electrogram sensed by a medical device via a plurality of electrodes; determining whether one or more of false pause detection criteria are satisfied based on the cardiac electrogram, wherein the one or more of false pause detection criteria comprise: at least one criterion for relative flatness of amplitude values of the cardiac electrogram in a time interval between a last pre-pause beat and a pause detection time; classifying the pause-triggered episode as one of a plurality of classifications based on the determination of whether the false pause detection criterion is satisfied; and output an indication of the classification of the pause-triggered episode to a user display device.

In another example, a non-transitory computer-readable storage medium comprises program instructions that, when executed by processing circuitry of a medical system, cause the processing circuitry to receive a cardiac electrogram of a pause-triggered episode, the cardiac electrogram sensed by a medical device via a plurality of electrodes; determine whether one or more of false pause detection criteria are satisfied based on the cardiac electrogram, wherein the one or more of false pause detection criteria comprise: at least one criterion for relative flatness of amplitude values of the cardiac electrogram in a time interval between a last pre-pause beat and a pause detection time; classify the pause-triggered episode as one of a plurality of classifications based on the determination of whether the false pause detection criterion is satisfied; and output an indication of the classification of the pause-triggered episode to a user display device.

The summary is intended to provide an overview of the subject matter described in this disclosure. It is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages will be apparent from the description and drawings, and from the claims.

BRIEF DESCRIPTION OF THE DRAWINGS

FIG. 8A illustrates an example cardio electrogram for a true pause episode and FIG. 8B illustrates an example cardio electrogram for a false pause episode.

FIG. 9A illustrates an example cardio electrogram of a true pause episode and a time interval for a false pause detection criterion. FIG. 9B illustrates an example cardio electrogram of a false pause episode and a time interval for a false pause detection criterion.

Like reference characters denote like elements throughout the description and figures.

DETAILED DESCRIPTION

Figure 1:
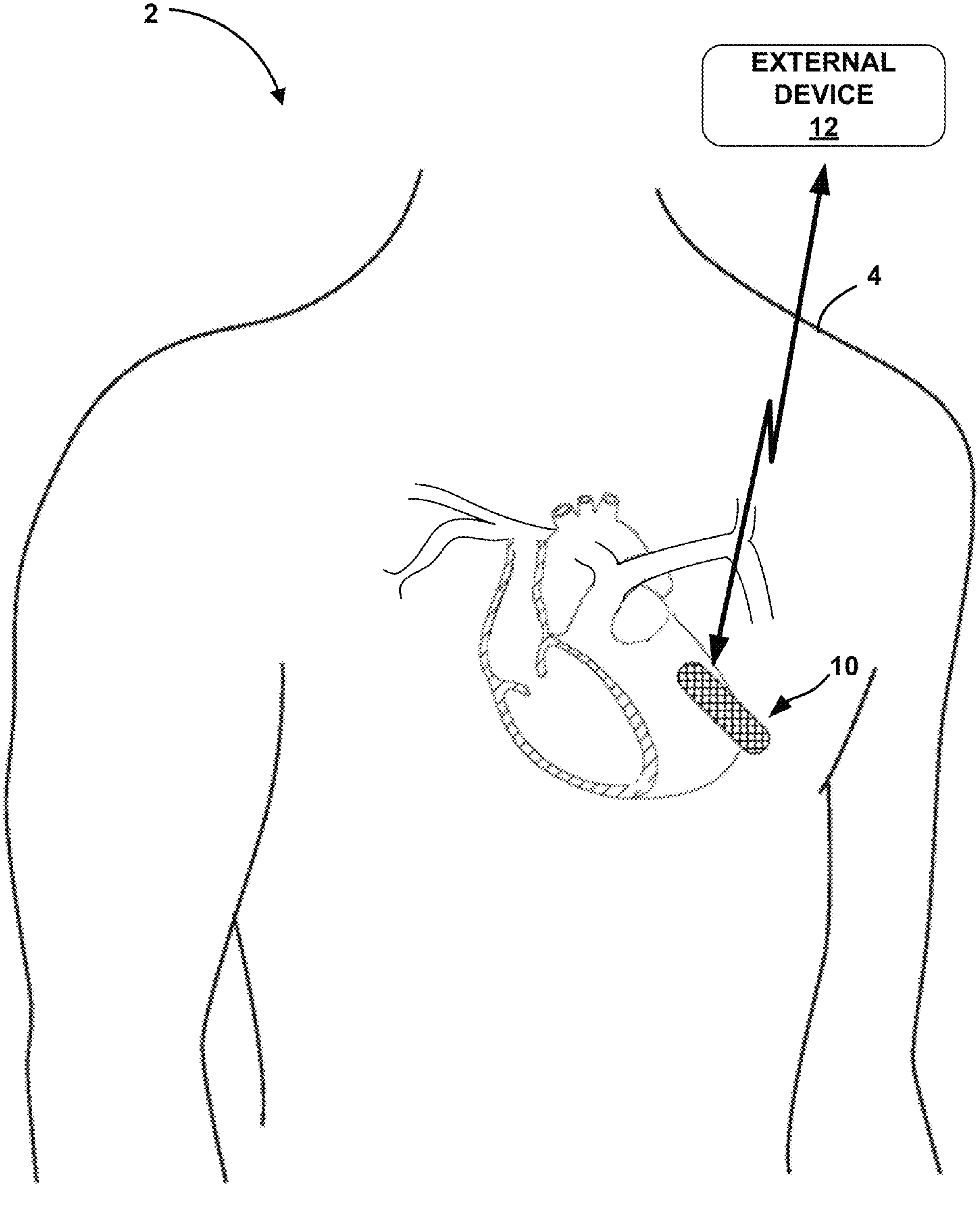
FIG. 1 illustrates the environment of an example medical system in conjunction with a patient.

A variety of types of medical devices sense and/or evaluate cardiac EGMs. Some medical devices that sense cardiac EGMs are non-invasive, e.g., using a plurality of electrodes placed in contact with external portions of the patient, such as at various locations on the skin of the patient. The electrodes used to monitor the cardiac EGM in these non-invasive processes may be attached to the patient using an adhesive, strap, belt, or vest, as examples, and electrically coupled to a monitoring device, such as an electrocardiograph, Holter monitor, or other electronic device. The electrodes are configured to sense electrical signals associated with the electrical activity of the heart or other cardiac tissue of the patient, and to provide these sensed electrical signals to the electronic device for further processing and/or display of the electrical signals. The non-invasive devices and methods may be utilized on a temporary basis, for example to monitor a patient during a clinical visit, such as during a doctor's appointment, or for example for a predetermined period of time, for example for one day (twenty-four hours), or for a period of several days.

External devices that may be used to non-invasively sense and monitor cardiac EGMs include wearable devices with electrodes configured to contact the skin of the patient, such as patches, watches, or necklaces. One example of a wearable physiological monitor configured to sense a cardiac EGM is the SEEQ™ Mobile Cardiac Telemetry System, available from Medtronic plc, of Dublin, Ireland. Such external devices may facilitate relatively longer-term monitoring of patients during normal daily activities, and may periodically transmit collected data to a network service, such as the Medtronic Carelink™ Network.

Implantable medical devices (IMDs) also sense and monitor cardiac EGMs. The electrodes used by IMDs to sense cardiac EGMs are typically integrated with a housing of the IMD and/or coupled to the IMD via one or more elongated leads. Example IMDs that monitor cardiac EGMs include pacemakers and implantable cardioverter-defibrillators, which may be coupled to intravascular or extravascular leads, as well as pacemakers with housings configured for implantation within the heart, which may be leadless. An example of pacemaker configured for intracardiac implantation is the Micra™ Transcatheter Pacing System, available from Medtronic plc. Some IMDs that do not provide therapy, e.g., implantable patient monitors, sense cardiac EGMs. One example of such an IMD is the Reveal LINQ™ Insertable Cardiac Monitor, available from Medtronic plc, which may be inserted subcutaneously. Such IMDs may facilitate relatively longer-term monitoring of patients during normal daily activities, and may periodically transmit collected data to a network service, such as the Medtronic Carelink™ Network.

Regardless of which type or types of devices are used, a noise signal, which may be referred to as an artifact, may appear in the cardiac EGM and interfere with sensing of depolarizations, causing one or more normal beats to go undetected by the medical device and missing from the cardiac EGM. The time duration of the noise signal may extend over a portion of a normal timeframe for a cardiac cycle of the heart, or may extend over a time span during which multiple cardiac cycles may be expected to have occurred. Such noise signals may be more prevalent when cutaneous, subcutaneous, or extravascular electrodes are used to sense the cardiac EGM, e.g., due to temporary change in contact between at least one of the electrodes and the tissue where the electrode is located due to relative motion of the electrode and tissue. In some examples, the noise signal manifests as a baseline drift of the cardiac EGM, and may include a portion that decays back towards the steady-state baseline.

The presence of a noise signal, artifacts, or undetected beats in a sensed cardiac EGM may cause circuitry for detect a false pause-triggered episode. In addition, the amplitude of the cardiac signals within the sensed cardiac EGM may vary over time, e.g., due to respiration. Such cardiac signal amplitude variation may also be more prevalent in cardiac EGMs sensed using cutaneous, subcutaneous, or extravascular electrodes. Variation in cardiac signal amplitude may also cause detections of pause episodes that turn out to be false pause episodes.

The false pause-triggered episodes may be inserted into a queue for manual review (e.g., by a clinician), increasing the burden of episode review. These types of variations in cardiac signal amplitude may lead to improper analysis of the actual cardiac activity occurring with respect to the patient being monitored, for example, by triggering a false-positive indication of a cardiac event, such as asystole, that is not actually occurring in the patient. Such false-positive indications could lead to incorrect assessment of the patient condition, including provision of therapy and/or sending false alerts to medical personnel responsible for the care of the patient being monitored. Low pass filtering of the cardiac EGM will generally not help solve these problems because these types of noise signals and amplitude variations may occur at frequencies near or below that of the cardiac signals.

Medical systems/devices according to this disclosure implement techniques for identifying false detection of pause-triggered episode in cardiac EGMs by, for example, detecting the presence of noise signals, artifacts, undetected beats, and cardiac signal amplitude variations. In some examples, processing circuitry of the systems analyzes a cardiac EGM associated with an identified pause episode to determine whether one or more false pause detection criterion are satisfied. Each false pause detection criterion may be configured to detect one or more indicators of noise, artifacts, undetected beats and/or amplitude variations in the cardiac EGM. These indicators were found to be predictive of false pauses and are based upon features corresponding to a normal beat count, a noise status of the last pre-pause beat, and a relative flatness of the EGM signal in a portion of the episode that satisfied one or more pause detection criteria or that a medical device otherwise identified as a pause, referred to as a pause interval, e.g., between the last pre-pause beat and the point of the pause detection.

In some examples, processing circuitry of a medical system/device performs this analysis in response to a cardiac EGM received from another device, for example, after an initial pause detection criterion is satisfied. The medical system/device may determine whether to designate the cardiac EGM for high priority, normal priority, or low priority review based on the analysis. In some examples, the processing circuitry of the medical system classifies the episode as a true pause episode with high priority in response to a determination that none of the one or more false pause-triggered episode detection criterion are satisfied. On the other hand, if there is a determination that at least one false pause-triggered episode detection criterion is satisfied, the processing circuitry of the medical system classifies the episode as a false pause episode. Depending upon the one or more false pause-triggered episode detection criterion that is/are satisfied, the processing circuitry may further classify the false pause episode as either low priority or normal priority. At least one additional criterion may be employed for the classification of the false pause episode as either low priority or normal priority after application of at least one false pause detection criterion to determine whether the pause-triggered episode is a true pause episode or a false episode.

The processing circuitry may perform the techniques of this disclosure substantially in real-time in response to the detection of pause, or during a later review of cardiac EGM data for episodes that were identified as pause. In either case, the processing circuitry may include the processing circuitry of medical device that detected the pause episode and/or processing circuitry of another device, such as a local or remote computing device which retrieved the episode data from the medical device. In this manner, the techniques of this disclosure may advantageously enable improved accuracy in the identification of true pause and, consequently, better evaluation of the condition of the patient.

Some examples of the following disclose a medical system and technique for prioritizing cardiac EGM data in a review process for pause-triggered electrogram episodes after an initial detection. One example discloses at least one medical system and technique for classifying pause-triggered electrogram episodes as either "a true pause with high priority" or a "false pause" and then classifying false pause-triggered electrogram episodes as either "a false pause with normal priority" or "a false pause with low priority" and placing cardiac EGM data in corresponding review queues such that the cardiac EGM data placed in a high priority queue is reviewed first. For example, cardiac EGM data is placed in the high-priority queue based on the number of beats in the episode, the noise status of the last pre-pause beat, and the relative flatness of the signal within a pause interval. In particular, the medical system and technique will flag the cardiac EGM data as high-priority if the total number of beats in the episode window is above a threshold, the beat registered at a second immediately preceding the pause interval is not a noisy beat, and the signal is relatively flat within the pause interval of the episode window.

To define relative flatness within the pause interval, the medical system and technique may analyze one or more amplitude criteria such as a criterion requiring a positive final difference value between an amplitude difference (e.g., the difference between the maximum and minimum amplitudes) at another time interval and an amplitude difference of the pause interval. Another criterion may indicate a minimum number of samples crossing an amplitude threshold (e.g., in the pause interval). As an example, the medical system and technique will flag the cardiac EGM data as low priority if any of the following conditions are satisfied: 1) a number of normal beats in the 45-second episode window is less than 20; 2) a number of samples in the 2.5 second pause interval crossing a threshold is greater than 2 and the beat immediately before the medical system and technique detected pause period is a noisy beat; 3) the number of normal beats in the 45 second episode window is less than 30 and the final difference value is less than 2000; or 4) the final difference value is less than −600.

FIG. 1 illustrates the environment of an example medical system 2 in conjunction with a patient 4, in accordance with one or more techniques of this disclosure. The example techniques may be used with an IMD 10, which may be in wireless communication with at least one of external device 12 and other devices not pictured in FIG. 1. In some examples, IMD 10 is implanted outside of a thoracic cavity of patient 4 (e.g., subcutaneously in the pectoral location illustrated in FIG. 1). IMD 10 may be positioned near the sternum near or just below the level of the heart of patient 4, e.g., at least partially within the cardiac silhouette. IMD 10 includes a plurality of electrodes (not shown in FIG. 1), and is configured to sense a cardiac EGM via the plurality of electrodes. In some examples, IMD 10 takes the form of the LINQ™ ICM.

External device 12 may be a computing device with a display viewable by the user and an interface for providing input to external device 12 (i.e., a user input mechanism). In some examples, external device 12 may be a notebook computer, tablet computer, workstation, one or more servers, cellular phone, personal digital assistant, or another computing device that may run an application that enables the computing device to interact with IMD 10.

External device 12 is configured to communicate with IMD 10 and, optionally, another computing device (not illustrated in FIG. 1), via wireless communication. External device 12, for example, may communicate via near-field communication technologies (e.g., inductive coupling, NFC or other communication technologies operable at ranges less than 10-20 cm) and far-field communication technologies (e.g., radiofrequency (RF) telemetry according to the 802.11 or Bluetooth® specification sets, or other communication technologies operable at ranges greater than near-field communication technologies).

External device 12 may be used to configure operational parameters for IMD 10. External device 12 may be used to retrieve data from IMD 10. The retrieved data may include values of physiological parameters measured by IMD 10, indications of episodes of arrhythmia or other maladies detected by IMD 10, and physiological signals recorded by IMD 10. For example, external device 12 may retrieve cardiac EGM segments recorded by IMD 10 due to IMD 10 determining that an episode of pause or another malady occurred during the segment. As will be discussed in greater detail below with respect to FIG. 5, one or more remote computing devices may interact with IMD 10 in a manner similar to external device 12, e.g., to program IMD 10 and/or retrieve data from IMD 10, via a network.

Processing circuitry of medical system 2, e.g., of IMD 10, external device 12, and/or of one or more other computing devices, may be configured to perform the example techniques for identifying false detection of asystole of this disclosure. In some examples, the processing circuitry of medical system 2 analyzes a cardiac EGM sensed by IMD 10 and associated with an identified asystole episode to determine whether one or more of a plurality of false asystole detection criteria are satisfied. Each of the false asystole detection criteria may be configured to detect one or more indicators of noise, artifacts, and/or amplitude variations in the cardiac EGM. Although described in the context of examples in which IMD 10 that senses the cardiac EGM comprises an insertable cardiac monitor, example systems including one or more implantable or external devices of any type configured to sense a cardiac EGM may be configured to implement the techniques of this disclosure.

Figure 2:
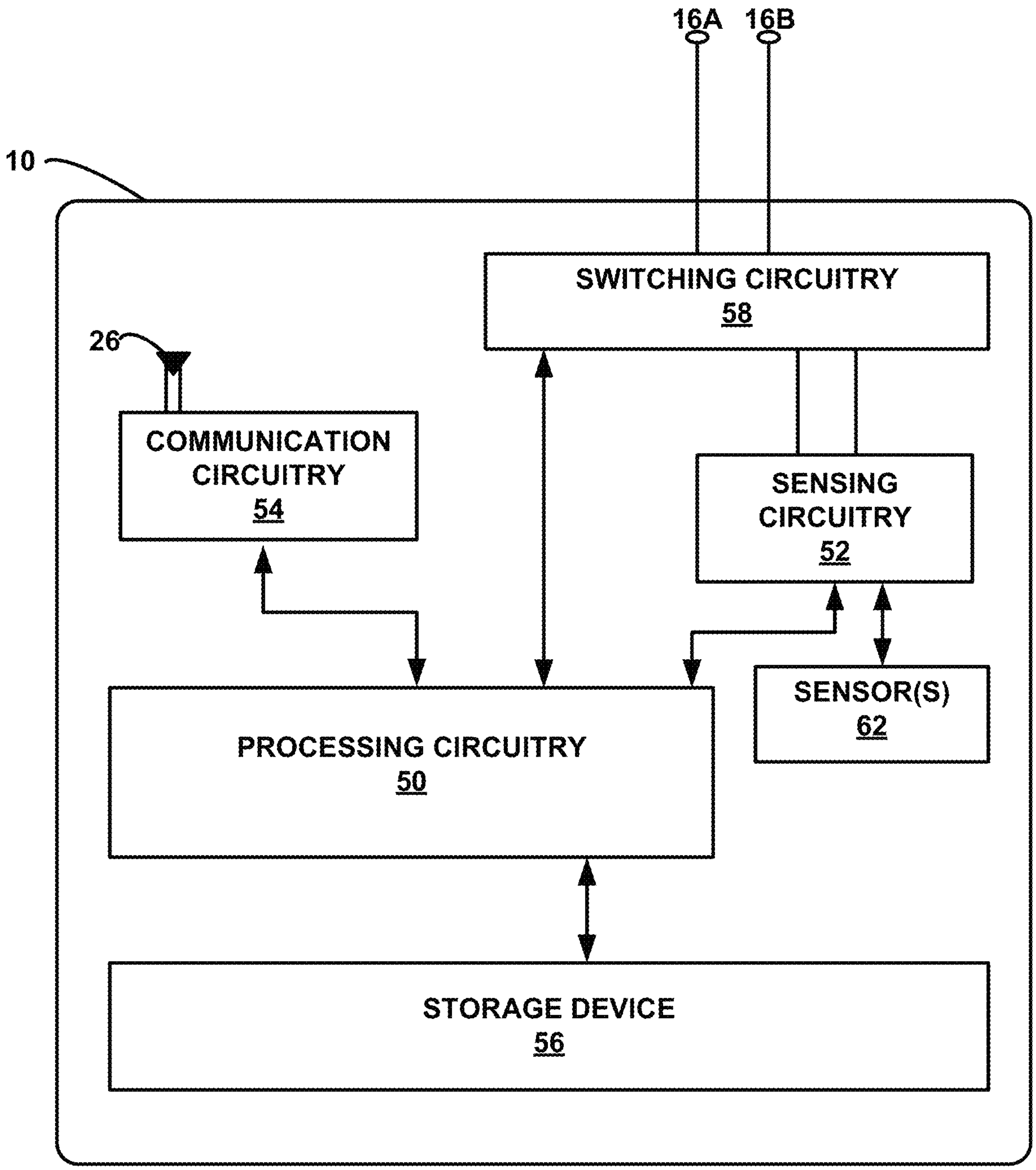
FIG. 2 is a functional block diagram illustrating an example configuration of the implantable medical device (IMD) of the medical system of FIG. 1.

FIG. 2 is a functional block diagram illustrating an example configuration of IMD 10 of FIG. 1 in accordance with one or more techniques described herein. In the illustrated example, IMD 10 includes electrodes 16A and 16B (collectively "electrodes 16"), antenna 26, processing circuitry 50, sensing circuitry 52, communication circuitry 54, storage device 56, switching circuitry 58, and sensors 62. Although the illustrated example includes two electrodes 16, IMDs including or coupled to more than two electrodes 16 may implement the techniques of this disclosure in some examples.

Processing circuitry 50 may include fixed function circuitry and/or programmable processing circuitry. Processing circuitry 50 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 50 may include multiple components, such as any combination of one or more microprocessors, one or more controllers, one or more DSPs, one or more ASICs, or one or more FPGAs, as well as other discrete or integrated logic circuitry. The functions attributed to processing circuitry 50 herein may be embodied as software, firmware, hardware or any combination thereof.

Sensing circuitry 52 may be selectively coupled to electrodes 16 via switching circuitry 58, e.g., to select the electrodes 16 and polarity, referred to as the sensing vector, used to sense a cardiac EGM, as controlled by processing circuitry 50. Sensing circuitry 52 may sense signals from electrodes 16, e.g., to produce a cardiac EGM, in order to facilitate monitoring the electrical activity of the heart. Sensing circuitry 52 also may monitor signals from sensors 62, which may include one or more accelerometers, pressure sensors, and/or optical sensors, as examples. In some examples, sensing circuitry 52 may include one or more filters and amplifiers for filtering and amplifying signals received from electrodes 16 and/or sensors 62.

Sensing circuitry 52 and/or processing circuitry 50 may be configured to detect cardiac depolarizations (e.g., P-waves or R-waves) when the cardiac EGM amplitude crosses a sensing threshold. In some examples, the sensing threshold is automatically adjustable over time using any of a variety of automatic sensing threshold adjustment techniques known in the art. For example, in response to detection of a cardiac depolarization, the sensing threshold for detecting a subsequent cardiac depolarization may decay from an initial value over a period of time. Sensing circuitry 52 and/or processing circuitry 50 may determine the initial value based on the amplitude of detected cardiac depolarization. The initial value and decay of the adjustable sensing threshold may be configured such that the sensing threshold is relatively higher soon after the detected cardiac depolarization when a subsequent depolarization is not expected, and decays to relatively lower values over time as the occurrence of a cardiac depolarization becomes more likely. For cardiac depolarization detection, sensing circuitry 52 may include a rectifier, filter, amplifier, comparator, and/or analog-to-digital converter, in some examples.

In some examples, sensing circuitry 52 may output an indication to processing circuitry 50 in response to sensing of a cardiac depolarization. In this manner, processing circuitry 50 may receive detected cardiac depolarization indicators corresponding to the occurrence of detected R-waves and P-waves in the respective chambers of heart. Processing circuitry 50 may use the indications of detected R-waves and P-waves for determining heart rate and detecting arrhythmias, such as tachyarrhythmias and asystole.

Communication circuitry 54 may include any suitable hardware, firmware, software or any combination thereof for communicating with another device, such as external device 12, another networked computing device, or another IMD or sensor. Under the control of processing circuitry 50, communication circuitry 54 may receive downlink telemetry from, as well as send uplink telemetry to external device 12 or another device with the aid of an internal or external antenna, e.g., antenna 26. In addition, processing circuitry 50 may communicate with a networked computing device via an external device (e.g., external device 12) and a computer network, such as the Medtronic CareLink® Network. Antenna 26 and communication circuitry 54 may be configured to transmit and/or receive signals via inductive coupling, electromagnetic coupling, Near Field Communication (NFC), Radio Frequency (RF) communication, Bluetooth, WiFi, or other proprietary or non-proprietary wireless communication schemes.

In some examples, storage device 56 includes computer-readable instructions that, when executed by processing circuitry 50, cause IMD 10 and processing circuitry 50 to perform various functions attributed to IMD 10 and processing circuitry 50 herein. Storage device 56 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media. Storage device 56 may store, as examples, programmed values for one or more operational parameters of IMD 10 and/or data collected by IMD 10 for transmission to another device using communication circuitry 54. Data stored by storage device 56 and transmitted by communication circuitry 54 to one or more other devices may include episode data for suspected or potential pause-triggered episodes and/or indications that suspected or potential pause-triggered episodes satisfied one or more false pause-triggered episode detection criteria.

Processing circuitry 50 may detect a pause-triggered episode based on determining that the cardiac electrogram satisfies an initial pause-triggered episode detection criterion. Presence in a cardiac EGM signal of a pause (or an absence of a cardiac depolarization for a predetermined period of time (e.g., three seconds) without registering a normal beat) leads to an initial detection of the pause-triggered episode. In such examples, processing circuitry 50 may determine that the cardiac EGM satisfies the initial pause-triggered episode detection criterion based on reaching the predetermined period of time from detection of a cardiac depolarization without receiving another cardiac depolarization indication from sensing circuitry 52.

Sensing circuitry 52 may also provide one or more digitized cardiac EGM signals to processing circuitry 50 for analysis, e.g., for use in cardiac rhythm discrimination, and/or for analysis to determine whether the initial pause-triggered episode detection criteria are satisfied. In some examples, based on satisfaction of the initial pause-triggered episode detection criterion, processing circuitry 50 may store a segment of the digitized cardiac EGM corresponding to the suspected pause-triggered episode as episode data in storage device 56. The digitized cardiac EGM segment may include samples of the cardiac EGM spanning the period of time for which sensing circuitry 52 did not indicate detection of a depolarization, as well as a period of time before and/or after this period of time during which depolarizations were detected. Processing circuitry 50 of IMD 10, and/or processing circuitry of another device that retrieves the episode data from IMD 10, may analyze the cardiac EGM segment to determine whether one or more false asystole detection criteria are satisfied according to the techniques of this disclosure.

Sensing circuitry 52 may also provide one or more digitized cardiac EGM signals to external device 12 for real-time or off-line analysis, e.g., for use in cardiac rhythm discrimination, and/or for real-time or off-line analysis to determine whether one or more false pause-triggered episode detection criteria are satisfied according to the techniques of this disclosure. Sensing circuitry 52 may also provide cardiac EGM data to external device 12 for real-time or off-line analysis, e.g., for use in cardiac rhythm discrimination, and/or for real-time or off-line analysis to determine whether one or more false pause-triggered episode detection criteria are satisfied according to the techniques of this disclosure. As an alternative, sensing circuitry 52 may also provide one or more digitized cardiac EGM signals to processing circuitry 50 for analysis, e.g., for use in cardiac rhythm discrimination, and/or for analysis to determine whether one or more false pause-triggered episode detection criteria are satisfied.

Communication circuitry 54 may provide cardiac EGM data to external device 12 for real-time or off-line analysis, e.g., for use in cardiac rhythm discrimination, and/or for real-time or off-line analysis to determine whether one or more false pause-triggered episode detection criteria are satisfied according to the techniques of this disclosure.

Figure 3:
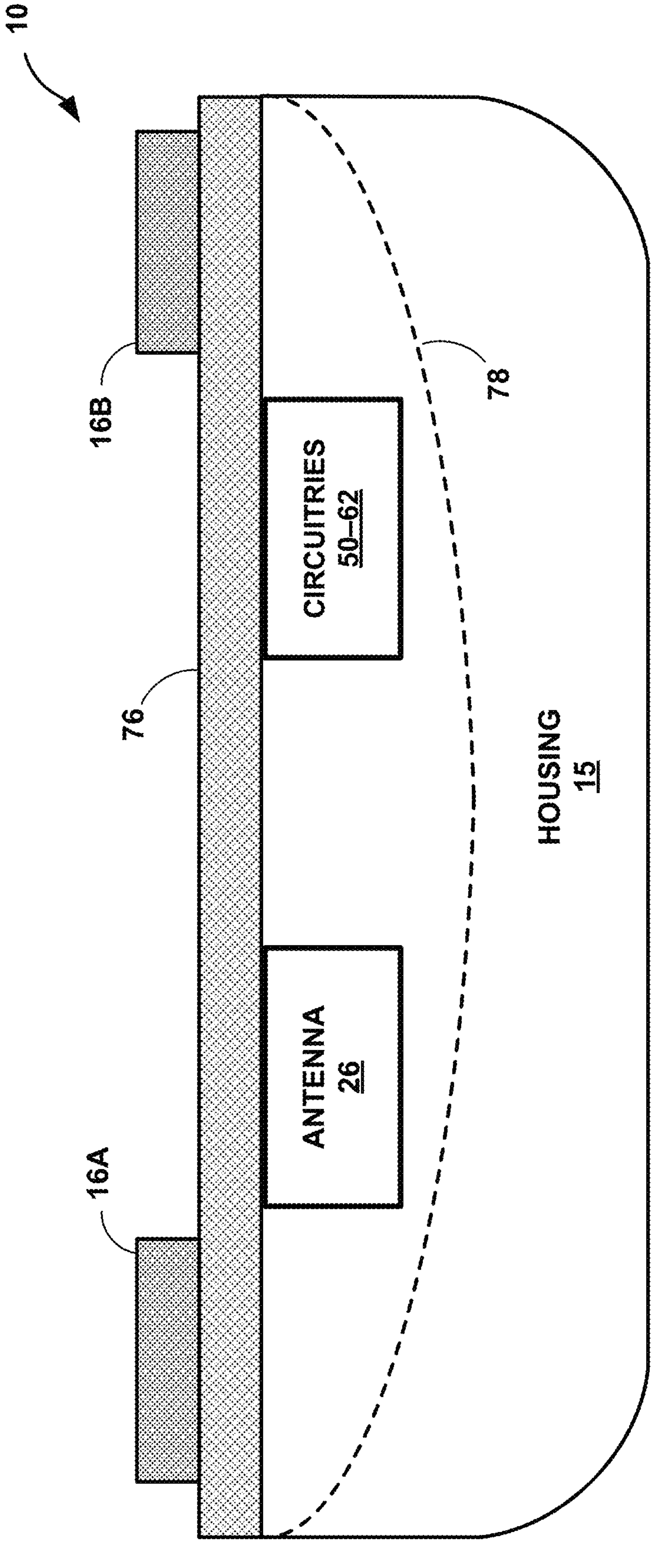
FIG. 3 is a conceptual side-view diagram illustrating an example configuration of the IMD of FIGS. 1 and 2.

FIG. 3 is a conceptual side-view diagram illustrating an example configuration of IMD 10 of FIGS. 1 and 2. In the example shown in FIG. 3, IMD 10 may include a leadless, subcutaneously-implantable monitoring device having a housing 15 and an insulative cover 76. Electrode 16A and electrode 16B may be formed or placed on an outer surface of cover 76. Circuitries 50-62, described above with respect to FIG. 2, may be formed or placed on an inner surface of cover 76, or within housing 15. In the illustrated example, antenna 26 is formed or placed on the inner surface of cover 76, but may be formed or placed on the outer surface in some examples. In some examples, insulative cover 76 may be positioned over an open housing 15 such that housing 15 and cover 76 enclose antenna 26 and circuitries 50-62, and protect the antenna and circuitries from fluids such as body fluids.

One or more of antenna 26 or circuitries 50-62 may be formed on the inner side of insulative cover 76, such as by using flip-chip technology. Insulative cover 76 may be flipped onto a housing 15. When flipped and placed onto housing 15, the components of IMD 10 formed on the inner side of insulative cover 76 may be positioned in a gap 78 defined by housing 15. Electrodes 16 may be electrically connected to switching circuitry 58 through one or more vias (not shown) formed through insulative cover 76. Insulative cover 76 may be formed of sapphire (i.e., corundum), glass, parylene, and/or any other suitable insulating material. Housing 15 may be formed from titanium or any other suitable material (e.g., a biocompatible material). Electrodes 16 may be formed from any of stainless steel, titanium, platinum, iridium, or alloys thereof. In addition, electrodes 16 may be coated with a material such as titanium nitride or fractal titanium nitride, although other suitable materials and coatings for such electrodes may be used.

Figure 4:
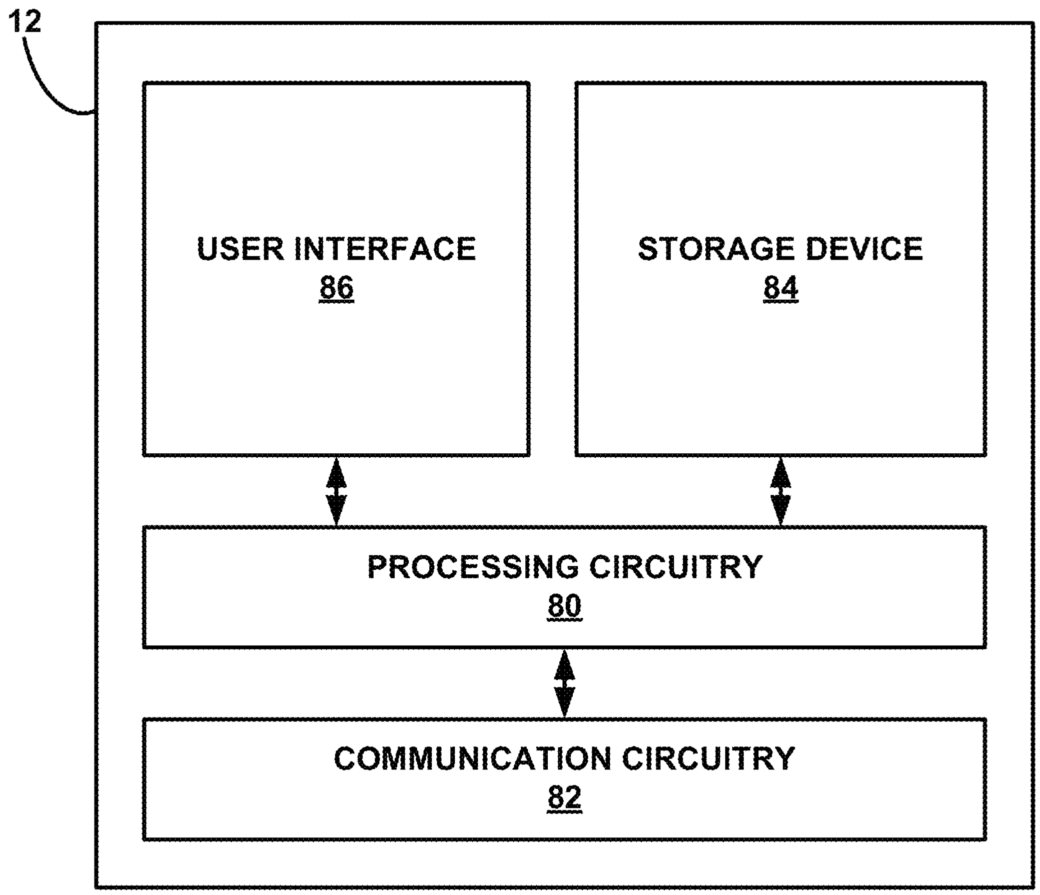
FIG. 4 is a functional block diagram illustrating an example configuration of the external device of FIG. 1.

FIG. 4 is a block diagram illustrating an example configuration of components of external device 12. In the example of FIG. 4, external device 12 includes processing circuitry 80, communication circuitry 82, storage device 84, and user interface 86.

Processing circuitry 80 may include one or more processors that are configured to implement functionality and/or process instructions for execution within external device 12. For example, processing circuitry 80 may be capable of processing instructions stored in storage device 84. Processing circuitry 80 may include, for example, microprocessors, DSPs, ASICs, FPGAs, or equivalent discrete or integrated logic circuitry, or a combination of any of the foregoing devices or circuitry. Accordingly, processing circuitry 80 may include any suitable structure, whether in hardware, software, firmware, or any combination thereof, to perform the functions ascribed herein to processing circuitry 80.

Communication circuitry 82 may include any suitable hardware, firmware, software or any combination thereof for communicating with another device, such as IMD 10. Under the control of processing circuitry 80, communication circuitry 82 may receive downlink telemetry from, as well as send uplink telemetry to, IMD 10, or another device. Communication circuitry 82 may be configured to transmit or receive signals via inductive coupling, electromagnetic coupling, NFC, RF communication, Bluetooth, WiFi, or other proprietary or non-proprietary wireless communication schemes. Communication circuitry 82 may also be configured to communicate with devices other than IMD 10 via any of a variety of forms of wired and/or wireless communication and/or network protocols.

Storage device 84 may be configured to store information within external device 12 during operation. Storage device 84 may include a computer-readable storage medium or computer-readable storage device. In some examples, storage device 84 includes one or more of a short-term memory or a long-term memory. Storage device 84 may include, for example, RAM, DRAM, SRAM, magnetic discs, optical discs, flash memories, or forms of EPROM or EEPROM. In some examples, storage device 84 is used to store data indicative of instructions for execution by processing circuitry 80. Storage device 84 may be used by software or applications running on external device 12 to temporarily store information during program execution.

Data exchanged between external device 12 and IMD 10 may include operational parameters. External device 12 may transmit data including computer readable instructions which, when implemented by IMD 10, may control IMD 10 to change one or more operational parameters and/or export collected data. For example, processing circuitry 80 may transmit an instruction to IMD 10 which requests IMD 10 to export collected data (e.g., asystole episode data) to external device 12. In turn, external device 12 may receive the collected data from IMD 10 and store the collected data in storage device 84. Processing circuitry 80 may implement any of the techniques described herein to analyze cardiac EGMs received from IMD 10, e.g., to determine whether one or more false pause-triggered episode detection criterion are satisfied.

A user, such as a clinician or patient 4, may interact with external device 12 through user interface 86. User interface 86 includes a display (not shown), such as a liquid crystal display (LCD) or a light emitting diode (LED) display or other type of screen, with which processing circuitry 80 may present information related to IMD 10, e.g., cardiac EGMs, indications of detections of arrhythmia episodes, and indications of determinations that one or more false pause-triggered episode detection criterion were satisfied. In addition, user interface 86 may include an input mechanism configured to receive input from the user. The input mechanisms may include, for example, any one or more of buttons, a keypad (e.g., an alphanumeric keypad), a peripheral pointing device, a touch screen, or another input mechanism that allows the user to navigate through user interfaces presented by processing circuitry 80 of external device 12 and provide input. In other examples, user interface 86 also includes audio circuitry for providing audible notifications, instructions or other sounds to the user, receiving voice commands from the user, or both.

Between external device 12 and IMD 10, IMD may transmit cardiac EGM data recording cardiac EGM signals and external device 12 may receive the cardiac EGM data and classify the cardiac EGM signals into a plurality of classifications. Processing circuitry 80 may apply the one or more false pause-triggered episode detection criteria to determine whether a pause-triggered episode is a false pause or a true pause and then to classify the false pause or the true pause as a low priority, a normal priority, or a high priority episode for a review process. In some examples, the one or more false pause-triggered episode detection criterion include at least one amplitude criterion configured to evaluate a relative flatness of at least a portion of the pause-triggered episode. The cardiac EGM signal indicates electrical activity of a heart and during a pause interval, amplitude values remain relatively flat in true pauses but varies considerably in false pauses.

In some examples, the processing circuitry 80 of the external device 12 determines whether to provide or withhold an indication (e.g., to a clinician or other user) that the patient experienced a true pause-triggered episode (or simply pause episode) based on the analysis. In some examples, the processing circuitry 80 of the external device determines whether to provide or withhold an indication (e.g., to a clinician or other user) that the patient experienced a false pause-triggered episode (or simply pause episode) based on the analysis.

Figure 5:
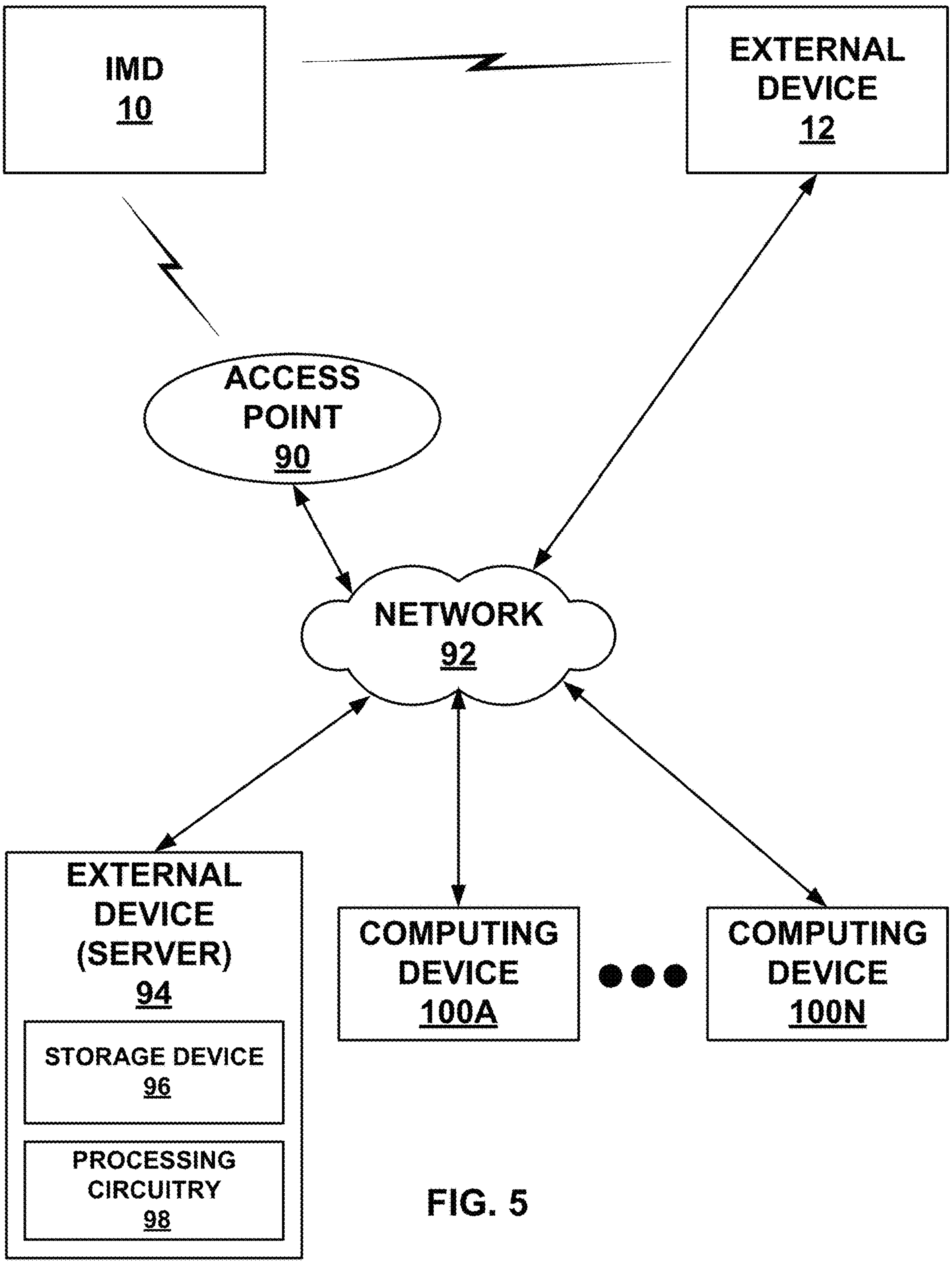
FIG. 5 is a block diagram illustrating an example system that includes an access point, a network, external computing devices, such as a server, and one or more other computing devices, which may be coupled to the IMD and external device of FIGS. 1-4.

FIG. 5 is a block diagram illustrating an example system that includes an access point 90, a network 92, external computing devices, such as a server 94, and one or more other computing devices 100A-100N (collectively, "computing devices 100"), which may be coupled to IMD 10 and external device 12 via network 92, in accordance with one or more techniques described herein. In this example, IMD 10 may use communication circuitry 54 to communicate with external device 12 via a first wireless connection, and to communicate with an access point 90 via a second wireless connection. In the example of FIG. 5, access point 90, external device 12, server 94, and computing devices 100 are interconnected and may communicate with each other through network 92.

Access point 90 may include a device that connects to network 92 via any of a variety of connections, such as telephone dial-up, digital subscriber line (DSL), or cable modem connections. In other examples, access point 90 may be coupled to network 92 through different forms of connections, including wired or wireless connections. In some examples, access point 90 may be a user device, such as a tablet or smartphone, that may be co-located with the patient. IMD 10 may be configured to transmit data, such as asystole episode data and indications that one or more false asystole detection criteria are satisfied, to access point 90. Access point 90 may then communicate the retrieved data to server 94 via network 92.

In some cases, server 94 may be configured to provide a secure storage site for data that has been collected from IMD 10 and/or external device 12. In some cases, server 94 may assemble data in web pages or other documents for viewing by trained professionals, such as clinicians, via computing devices 100. One or more aspects of the illustrated system of FIG. 5 may be implemented with general network technology and functionality, which may be similar to that provided by the Medtronic CareLink® Network.

In some examples, one or more of computing devices 100 may be a tablet or other smart device located with a clinician, by which the clinician may program, receive alerts from, and/or interrogate IMD 10. For example, the clinician may access data collected by IMD 10 through a computing device 100, such as when patient 4 is in in between clinician visits, to check on a status of a medical condition. In some examples, the clinician may enter instructions for a medical intervention for patient 4 into an application executed by computing device 100, such as based on a status of a patient condition determined by IMD 10, external device 12, server 94, or any combination thereof, or based on other patient data known to the clinician. Device 100 then may transmit the instructions for medical intervention to another of computing devices 100 located with patient 4 or a caregiver of patient 4. For example, such instructions for medical intervention may include an instruction to change a drug dosage, timing, or selection, to schedule a visit with the clinician, or to seek medical attention. In further examples, a computing device 100 may generate an alert to patient 4 based on a status of a medical condition of patient 4, which may enable patient 4 proactively to seek medical attention prior to receiving instructions for a medical intervention. In this manner, patient 4 may be empowered to take action, as needed, to address his or her medical status, which may help improve clinical outcomes for patient 4.

In the example illustrated by FIG. 5, server 94 includes a storage device 96, e.g., to store data retrieved from IMD 10, and processing circuitry 98. Although not illustrated in FIG. 5 computing devices 100 may similarly include a storage device and processing circuitry. Processing circuitry 98 may include one or more processors that are configured to implement functionality and/or process instructions for execution within server 94. For example, processing circuitry 98 may be capable of processing instructions stored in storage device 96. Processing circuitry 98 may include, for example, microprocessors, DSPs, ASICs, FPGAs, or equivalent discrete or integrated logic circuitry, or a combination of any of the foregoing devices or circuitry. Accordingly, processing circuitry 98 may include any suitable structure, whether in hardware, software, firmware, or any combination thereof, to perform the functions ascribed herein to processing circuitry 98. Processing circuitry 98 of server 94 and/or the processing circuitry of computing devices 100 may implement any of the techniques described herein to analyze cardiac EGMs received from IMD 10, e.g., to determine whether the pause-triggered episode and the one or more false pause-triggered episode detection criterion are satisfied.

Storage device 96 may include a computer-readable storage medium or computer-readable storage device. In some examples, storage device 96 includes one or more of a short-term memory or a long-term memory. Storage device 96 may include, for example, RAM, DRAM, SRAM, magnetic discs, optical discs, flash memories, or forms of EPROM or EEPROM. In some examples, storage device 96 is used to store data indicative of instructions for execution by processing circuitry 98.

Figure 6:
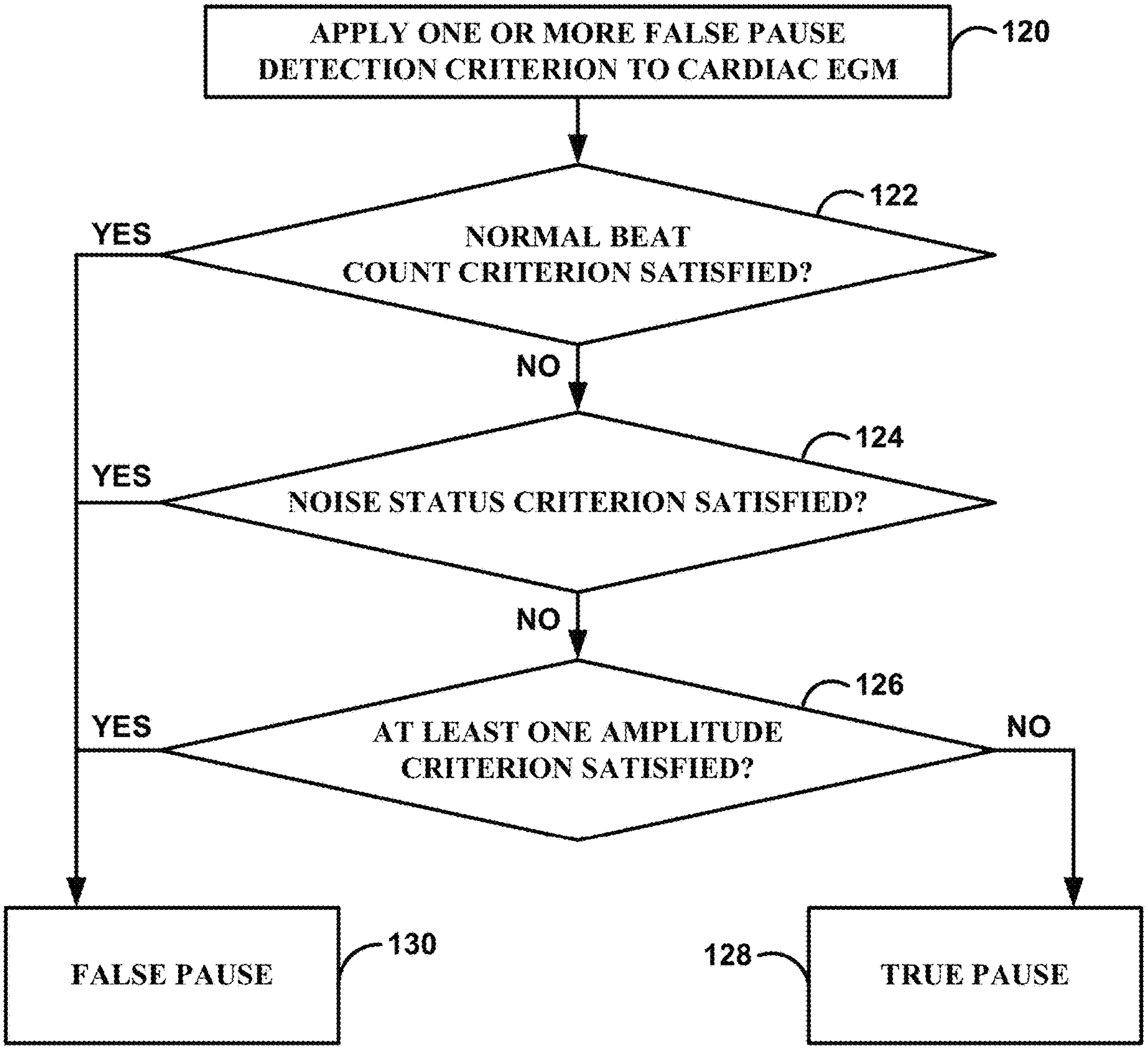
FIG. 6 is a flow diagram illustrating an example operation for determining whether an identification of a pause episode was false based on whether a plurality of false pause detection criteria is satisfied.

FIG. 6 is a flow diagram illustrating an example operation for determining whether an identification of a pause-triggered episode was false based on whether one or more false pause-triggered episode detection criterion are satisfied. Medical system 2 according to the illustrated examples of FIGS. 1-5 includes various computing hardware/software components of which some are medical devices communicably coupled to each other via a communication protocol.

In one example, processing circuitry 50 of example medical device IMD 10 determines that at least one pause-triggered episode detection criterion is satisfied based on a cardiac EGM sensed by sensing circuitry 52 of IMD 10. For example, as discussed in greater detail with respect to FIG. 2, processing circuitry 50 may determine that a threshold time interval, e.g., 2-3 seconds, has passed since sensing circuitry 52 identified a cardiac depolarization, e.g., R-wave, within the cardiac EGM.

Figure 7:
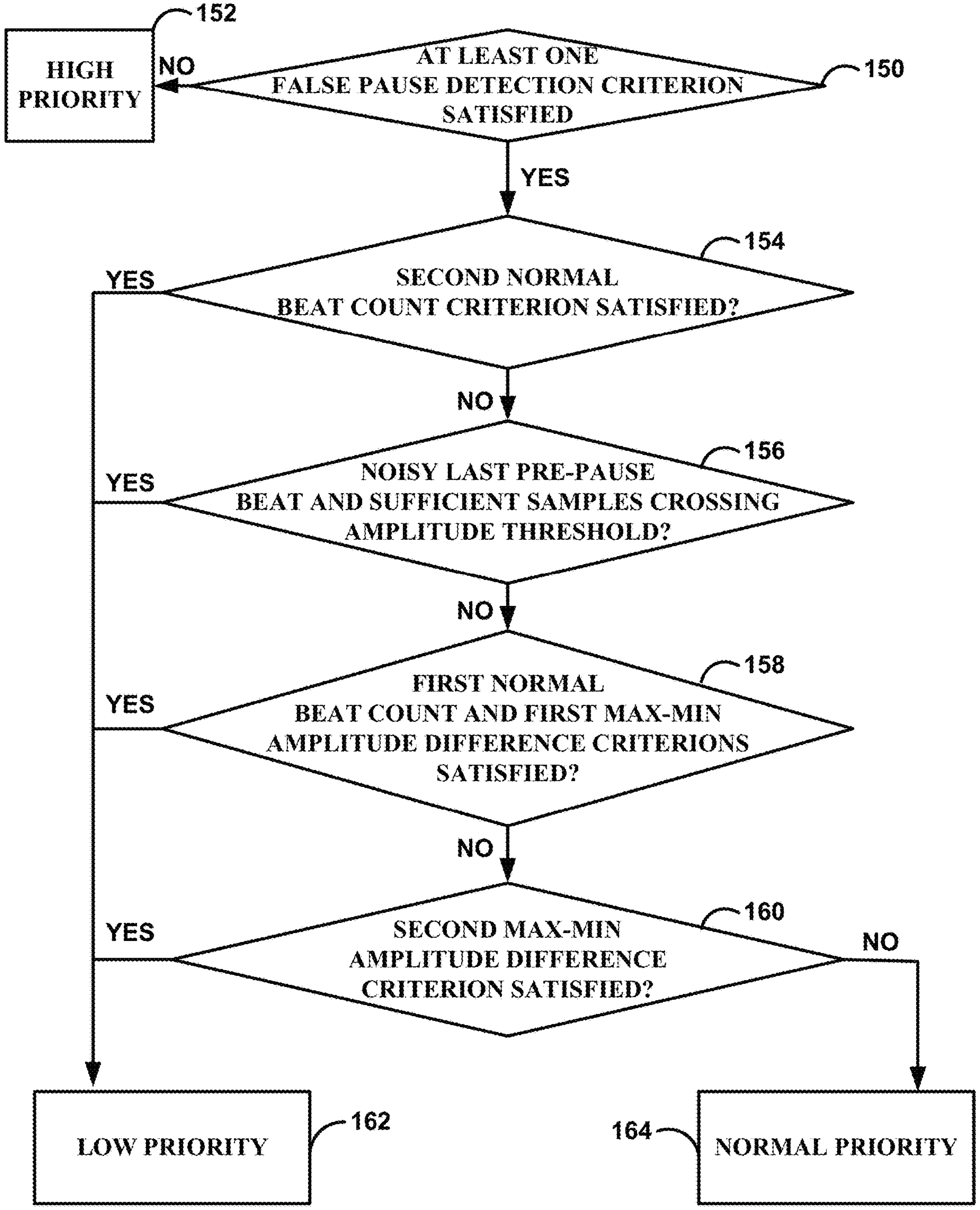
FIG. 7 is a flow diagram illustrating an example operation for determining whether an identification of an asystole episode was false based on whether a plurality of false asystole detection criteria is satisfied.

External device 12, another example medical device of medical system 2, includes processing circuitry 80 to receive the cardiac EGM and evaluate various corresponding data sets by applying one or more false pause-triggered episode detection criterion to those data sets (120). An example false pause-triggered episode detection criterion, as described herein, may include one or more conditions that, if satisfied, indicate a likely false pause-triggered episode. If none of the one or more false pause-triggered episode detection criterion are satisfied, the pause-triggered episode is most likely a true pause. In some instances, medical system 2 classifies the pause-triggered episode for a review process as depicted in FIG. 7.

To properly evaluate the cardiac EGM for a false positive, medical system 2 may apply three false pause-triggered episode detection criterion to the cardiac EGM, as illustrated by the example of FIG. 6. In the illustrated example, processing circuitry 80 determines whether an example false pause-triggered episode detection criterion comprising a normal beat count criterion is satisfied (122). The normal beat count criterion may indicate an insufficient number of normal beats in the pause-triggered episode. For example, processing circuitry 80 may determine whether the false pause-triggered episode detection criterion is satisfied with a threshold number of normal beats within a predetermined time period extending back from the most recent satisfaction of the pause-triggered episode detection criterion. In some examples, the episode includes cardiac EGM data for periods of time preceding and following an interval identified as a pause, and processing circuitry 80 may determine whether the false pause-triggered episode detection criterion is satisfied with the threshold number of normal beats the episode data exclusive of the interval identified as a pause.

One example threshold number of normal beats is a fixed, predetermined number while another example threshold may be determined as a ratio or percentage of a normal beat count to the total number of beats in the above-mentioned predetermined time period; for example, processing circuitry 80 may identify a pause-triggered episode as a false pause if the normal beat count is less than eighty (80)% of total beat count in that predetermined time period. Implementation of such a normal beat count criterion is based on an observation that false detection of a pause-triggered episode tends to occur when there is considerable noise, such as when there is an insufficient number of normal beats. Noise signals may occur in the cardiac EGM intermittently or with varying frequency based on, for example, changes in the condition of IMD 10 or patient 4. Consequently, there may be a greater likelihood that a recently detected pause is actually false (e.g., caused by noise) during a period in which a number of detected normal beats is insufficient (indicating that there may be noise in the EGM) than a period in which there is a sufficient number of detected normal beats. Requiring satisfaction for the normal beat count criterion, as in the example operation of FIG. 6, may avoid erroneous classification of a suspect pause-triggered episode as true pause by the false pause-triggered episode detection criteria.

In some examples, processing circuitry 80 analyzes the morphology of the cardiac EGM signal for each of the beats detected within the cardiac EGM, or a portion thereof. Processing circuitry 80 may classify each of the beats as normal or another classification based on the analysis. The morphological analysis may include a comparison of the cardiac EGM signal for each beat to one or more templates, e.g., a normal beat template.

In response to determining that the normal beat count criterion is not satisfied (NO branch of 122), processing circuitry 80 proceeds to apply a second false pause-triggered episode detection criterion of the three false pause-triggered episode detection criterion. If the normal beat count criterion is satisfied (YES branch of 122), the pause-triggered episode is most likely a false pause and the example operation of FIG. 6 ends (130). In the illustrated example, processing circuitry 80 determines whether the second false pause-triggered episode detection criterion comprising a noise status criterion is satisfied (124). The noise status criterion may indicate a noisy last pre-pause beat in the cardiac EGM, e.g., whether the morphological classification of the beat in the cardiac EGM immediately preceding the interval identified as a pause was noisy or otherwise not normal.

In response to determining that the noise status criterion is not satisfied (NO branch of 124), processing circuitry 80 proceeds to apply at least a third false pause-triggered episode detection criterion of the three false pause-triggered episode detection criterion. Based on whether the noise status criterion is satisfied (YES branch of 124), the pause-triggered episode is most likely a false pause and the example operation of FIG. 6 ends (130). In the illustrated example, processing circuitry 80 determines whether the third false pause-triggered episode detection criterion comprising at least one amplitude criterion is satisfied (126). Each amplitude criterion may include one or more conditions for determining a relative flatness of amplitude values in the cardiac EGM, specifically a first interval (i.e., a pause interval) between the last pre-pause beat and the pause-triggered episode detection. In some examples, the pause interval is an interval, having a defined threshold time (e.g., 3 seconds), during which no beats were detected, thus satisfying the pause detection criterion. The relative flatness is a measurement of amplitude variation in the first interval. Criterion for determining the relative flatness are described in further detail with respect to FIGS. 8A-8B and FIGS. 9A-B.

One example amplitude criterion is satisfied with a non-positive difference value between a comparison window max-min amplitude difference value and a candidate window max-min amplitude difference. The candidate window max-min amplitude difference value refers to a difference value between a maximum amplitude and a minimum amplitude within a time interval encompassing the pause (i.e., the pause interval). The comparison window max-min amplitude difference value refers to a difference value between a maximum amplitude and a minimum amplitude within another time interval in the same cardiac EGM for the episode containing normal beats. An alternative example amplitude criterion includes a threshold difference value of less than zero (0) or greater than twenty thousand (20,000) for the difference value between max-min amplitude difference values between the comparison window and the candidate window. If the example amplitude criterion is satisfied (YES branch of 126), the pause-triggered episode is a likely false pause.

Another example amplitude criterion is satisfied when a negligible number of samples (e.g., zero or one) in the pause interval cross a maximum amplitude limit. In one example, the other example amplitude criterion defines the maximum amplitude limit as a value equal to a maximum amplitude minus a first parameter where the first parameter is a threshold amplitude value. In another example, the other example amplitude criterion defines a second parameter as a threshold for the number of samples crossing the maximum amplitude limit. If the other example amplitude criterion is satisfied or both the example amplitude criterion and the other example amplitude criterion are satisfied (YES branch of 126), the pause-triggered episode is a likely false pause.

Based on the example operation of FIG. 6 ending (NO branch of 126), e.g., due to none of the false pause-triggered detection criteria being satisfied, or an insufficient number or combination of the false pause-triggered detection criteria being satisfied, processing circuitry 80 may classify the suspected or potential pause-triggered episode as a true pause-triggered episode (128). Based on the pause-triggered episode being classified as true, processing circuitry 80 may use the pause-triggered episode in further operations, such as calculating statistics, determining a condition of patient, or transmitting true episode data to other devices. If one or more of the at least one amplitude criterion are satisfied (YES branch of 126), processing circuitry 80 determines that the pause-triggered episode is a likely false pause and the example operation of FIG. 6 ends (130). Hence, if at least one of the above-mentioned three false pause-triggered episode detection criterion are satisfied, the pause-triggered episode is a likely false pause. Based on determining that the suspected pause-triggered episode is a false pause-triggered (130), processing circuitry 80 may use the false pause-triggered episode in further operations, such as calculating statistics of false episodes and transmitting false episode data to other devices, e.g., for consideration by a user of a modification of the operation of IMD 10 to avoid further false pause-triggered detection.

FIG. 7 is a flow diagram illustrating an example operation for classifying a pause-triggered episode based on whether false pause-triggered episode detection criteria are satisfied. According to the illustrated example of FIG. 7, processing circuitry 80 of external device 12 classifies the pause-triggered episode as either a high-priority, a normal priority, or a low priority pause.

In the illustrated example of FIG. 7, processing circuitry 80 determines whether at least one false pause-triggered episode detection criterion is satisfied (150). Processing circuitry 80 performs this determination by applying the at least one false pause-triggered episode detection criterion to various data sets associated with a cardiac EGM for the pause-triggered episode. The example operation of FIG. 6 illustrates an example determination by processing circuitry 80 where applying the first, second, and third false pause-triggered episode detection criterion determines whether the pause-triggered episode in the cardiac EGM is a likely false pause or a likely true pause. If none of the applicable false pause-triggered episode detection criterion are satisfied (NO branch of 150), processing circuitry 80 determines that the pause-triggered episode is likely a true pause and classifies the true pause-triggered episode as high priority (152); otherwise, processing circuitry 80 determines that the pause-triggered episode is likely a false pause and proceeds to further classify the pause-triggered episode by applying one or more additional false pause-triggered episode detection criterion (YES branch of 150). Processing circuitry 80, upon classifying the pause-triggered episode as a high priority pause episode, may proceed to inserting the high priority pause episode into a review queue at a position ahead of any normal or low priority pause-triggered episodes.

Processing circuitry 80 classifies the likely false pause-triggered episode as normal priority if none of four or more additional false pause-triggered episode detection criteria are satisfied and, on the other hand, classifies the likely false pause-triggered episode as low priority if at least one of the four or more additional criterion are satisfied. Hence, the four or more additional criterion may be considered classification criteria.

In the illustrated example of FIG. 7, for a first additional criterion, processing circuitry 80 determines whether a second normal beat count criterion is satisfied (154). In some instances, the first normal beat count criterion may include a threshold number of normal beats and the second normal beat count criterion may include even fewer normal beats. The second normal beat count criterion, like the first normal beat count criterion, may be satisfied when a number of detected normal beats is less than or equal to a second threshold. Similar to the first normal beat count criterion, the second threshold may be fixed number or a specific ratio or percentage of a normal beat count to a total beat count. While the first normal beat count criterion indicates a likely false pause, the second normal beat count criterion indicates an even more or highly likely false pause.

In response to the determination that the second normal beat count criterion is satisfied (YES branch of 154), processing circuitry 80 classifies the likely false pause-triggered episode as low priority (162). In response to the determination that the second normal beat count criterion is not satisfied (NO branch of 154), processing circuitry 80 proceeds to apply a second additional criterion having, as conditions, a noisy last pre-pause beat and sufficient number of samples (e.g., two (2)) crossing an amplitude limit (e.g., a maximum amplitude limit) (156). In some example, processing circuitry 80 accesses an amplitude threshold as a parameter and sets the amplitude limit as a difference between a maximum amplitude value and the parameter.

In response to the determination that the second additional criterion is not satisfied (NO branch of 156), processing circuitry 80 proceeds to apply a third additional criterion having, as conditions, the first normal beat count and the first max-min amplitude difference criterions (158). The first max-min amplitude difference criterion refers to a threshold difference value between the comparison window max-min amplitude difference value and the candidate window max-min amplitude difference. As described herein, the first max-min amplitude difference criterion is used as one of the false pause-triggered episode detection criterion for determining whether the pause-triggered episode is a false pause or a true pause. The candidate window refers to the pause time interval and the comparison window refers to the second non-overlapping time interval in the same cardiac EGM containing normal beats. Comparing amplitude values in these time intervals determines the relative flatness of the cardiac EGM data of the pause-triggered episode.

Satisfaction with these conditions by the likely false pause-triggered episode indicates to processing circuitry 80 that the third additional criterion is satisfied (YES branch of 158), resulting in classification of the likely false pause-triggered episode as low priority (162). An example of the first max-min amplitude difference criterion includes a threshold difference of less than 2000 for the difference value between maximum amplitude and minimum amplitude difference values in two different time intervals; satisfying the first max-min amplitude difference criterion depends on whether an actual difference between difference values of max-min amplitude difference values is less than or equal to the above threshold difference. Respective ones of the maximum amplitude and minimum amplitude values may be extracted from samples in the first time interval encompassing the likely false pause and from samples in the non-overlapping second time interval encompassing a number of seconds equal to the first time interval. Samples in the second time interval define a pattern (e.g., a measurement of amplitude variation such as flatness) for normal cardiac electrical activity. Comparing the first and second time intervals in terms of max-min amplitude value differences determines a relative flatness of the likely false pause-triggered episode.

Based on the determination that the third additional criterion is not satisfied (NO branch of 158), processing circuitry 80 applies a fourth additional criterion (160). One example of the fourth additional criterion includes a second max-mix amplitude difference threshold. Compared to the first max-mix amplitude difference threshold, the second max-mix amplitude difference criterion may be a lower threshold, satisfaction of which is even more indicative of a false pause due to relative flatness in amplitude values.

In response to the determination that the fourth additional criterion is satisfied (YES branch of 160), processing circuitry 80 determines that the likely false pause-triggered episode is to be classified as low priority and the example operation of FIG. 7 ends (162). Based on determining that the pause-triggered episode is a low priority false pause-triggered (162), processing circuitry 50 may prioritize other episodes over this false pause-triggered episode. In response to the determination that the fourth additional criterion is not satisfied (NO branch of 160), processing circuitry 80 determines that the likely false pause-triggered episode is to be classified as a normal priority false pause-triggered episode. Based on the example operation of FIG. 7 ending (NO branch of 160), e.g., due to none of the four additional criteria being satisfied, or an insufficient number or combination of the four additional criteria being satisfied, processing circuitry 50 may classify the pause-triggered episode as a normal priority false pause-triggered episode (164). Based on the pause-triggered episode being classified as normal priority, processing circuitry 50 may prioritize the pause-triggered episode over low priority pause-triggered episodes and below high priority pause-triggered episodes.

The order and flow of the operations illustrated in FIG. 6 and FIG. 7 are examples. In other examples according to this disclosure, more or fewer criteria may be considered, the false pause-triggered episode detection criteria and the additional classification criteria may be considered in a different order, or satisfaction of different numbers or combinations of false pause-triggered episode detection criteria may be required for a determination that the pause-triggered episode was false and different numbers or combinations of the additional classification criteria may be required for a determination that the pause-triggered episode should be prioritized as low priority or normal priority. Further, in some examples, processing circuitry may perform or not perform the methods of FIG. 6 and/or FIG. 7, or any of the techniques described herein, as directed by a user, e.g., via external device 12 or computing devices 100. For example, a patient, clinician, or other user may turn on or off functionality for identifying false asystole detection remotely (e.g., using Wi-Fi or cellular services) or locally (e.g., using an application provided on a patient's cellular phone or using a medical device programmer).

Additionally, although described in the context of an example in which external device 12, and processing circuitry 80 of external device 12, perform each of the portions of the example operation, the example operation of FIG. 6, as well as the example operation described herein with respect to FIG. 7, may be performed by any processing circuitry of any one or more devices of a medical system, e.g., any combination of one or more of processing circuitry 50 of IMD 10, processing circuitry 80 of external device 12, processing circuitry 98 of server 94, or processing circuitry of computing devices 100. In some examples, processing circuitry 50 of IMD 10 may determine whether a pause-triggered episode detection criterion is satisfied, and provide episode data for the pause-triggered episodes to another device. In such examples, processing circuitry of the other device, e.g., external device 12, server 94, or a computing device 100, may apply one or more false pause-triggered episode detection criterion to the episode data.

Figure 8A:
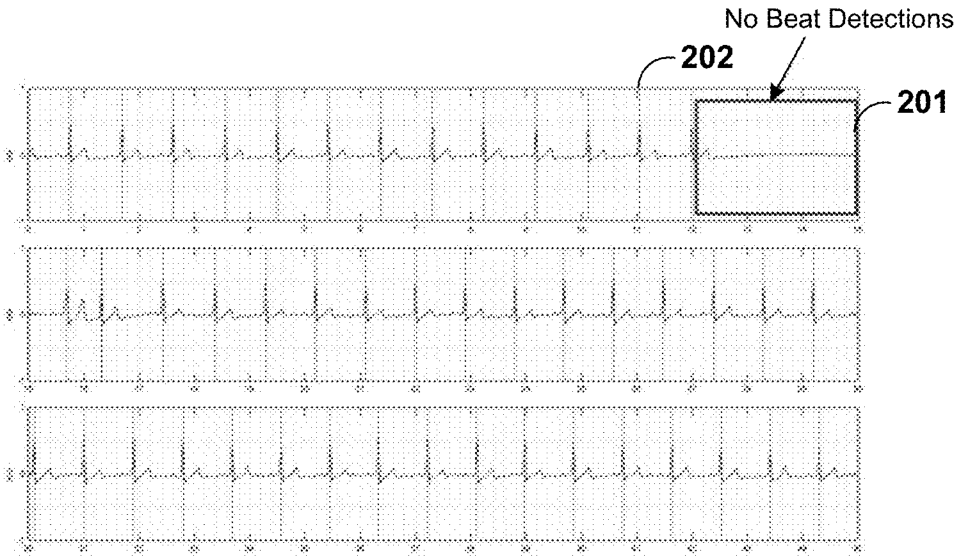
FIGS. 8A-B are illustrations of a cardio electrogram.
Figure 8B:
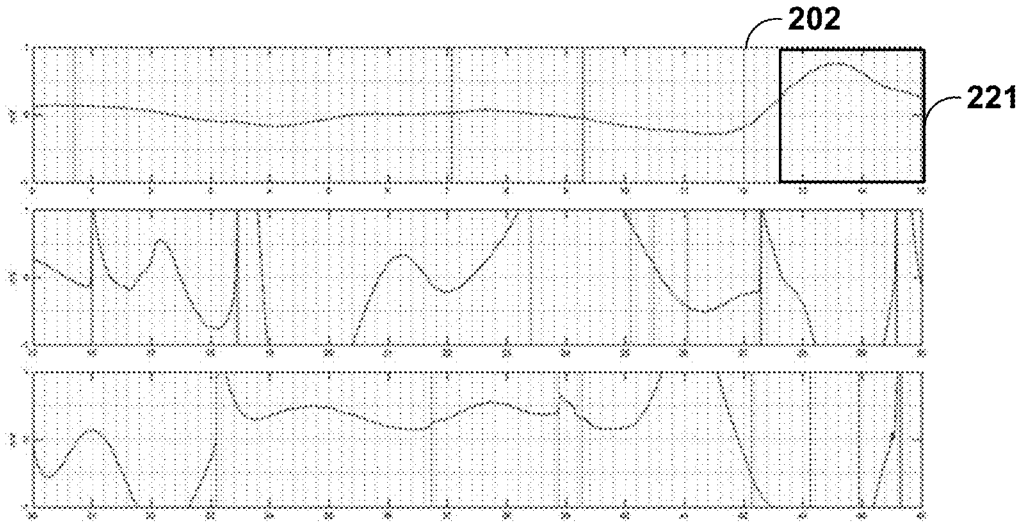

FIGS. 8A-B are illustrations of cardio electrograms 200 and 220. Both cardio electrograms 200, 220 depict possible pause-triggered episodes over corresponding time intervals. FIG. 8A illustrates an example cardiac electrogram (EGM) 200 for a true pause episode and FIG. 8B illustrates an example cardio EGM 220 for a false pause episode.

As illustrated in FIG. 8A, samples over three (3) second time interval 201 register zero (0) beat detections and flat amplitude values; in contrast to samples in three (3) second time interval 221, FIG. 8B illustrates zero (0) beat detections but with considerable amplitude variations (e.g., caused by noise) that indicate a false pause-triggered episode. The samples over three (3) second time interval 201 are relatively flat when compared to samples in other time intervals in cardiac EGM 200, whereas the samples over three (3) second time interval 221 vary considerably when compared to samples in other time intervals in cardiac EGM 220.

As described herein, relative flatness of amplitude values in a possible pause-triggered episode distinguishes episodes that are true pauses from those that are false pauses. One or more amplitude criterion defining the relative flatness in a first interval of the cardiac EGM may be used in one or more false pause-triggered episode criterion. Numerical values measuring the amplitude variations in the first interval (e.g., a max-min amplitude difference) may indicate a false pause if those values exceed a threshold. The threshold may be defined using amplitude values in a second time interval or may be pre-determined. If the amplitude variations exceed the threshold, the cardiac EGM most likely indicates a false pause.

Another example false pause-triggered episode criterion determines an insufficient number of normal beats as indicative of a false pause. This is, in part, because a true pause cannot be determined with insufficient normal beats. As depicted in FIG. 8A, sufficient number of normal beats are detected in cardiac EGM 200 and, as depicted in FIG. 8B, cardiac EGM 220 includes an insufficient normal beat count. Sufficiency may be defined as a normal beat count threshold (i.e., the first normal beat count criterion as described herein) and if the number of normal beats is less than or equal to that threshold, the pause is a likely false pause. In some instances, if the number of normal beats is less than or equal to a second lower threshold, the pause is most likely a false pause and is classified as low priority. Comparing FIG. 8A and FIG. 8B, a difference in a morphology of the beats can be visualized such that a morphological analysis would identify an insufficient number of normal beats in FIG. 8B.

Yet another example false pause-triggered episode criterion includes a noise status of a last pre-pause beat 202 that is indicative of a false pause. In some examples, a noisy last pre-pause beat indicates noise in the time interval encompassing the pause-triggered episodes. Samples and corresponding data sets in the time interval are not reliable and cannot be used in confirming a true pause.

Figure 9A:
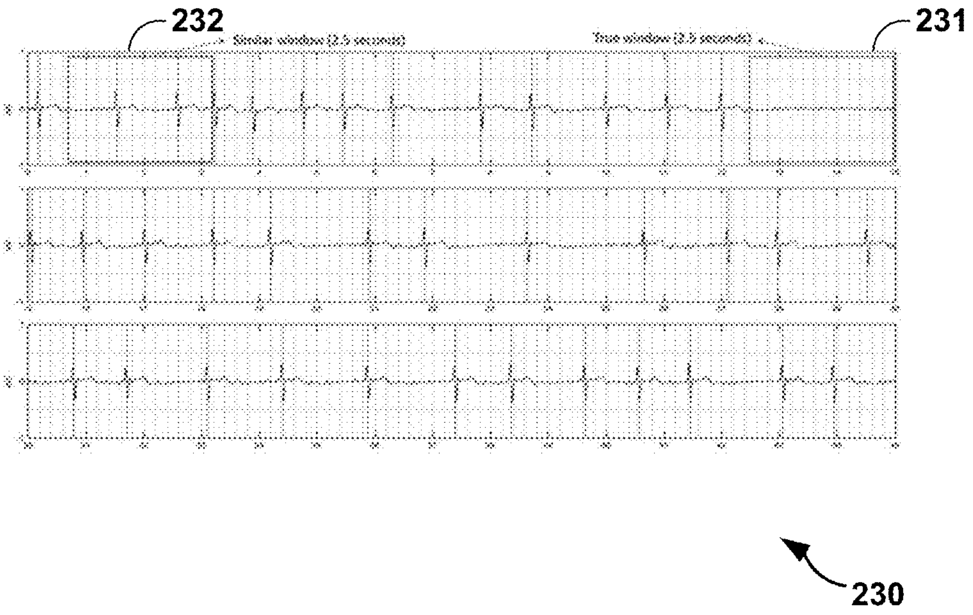
FIGS. 9A-B are both illustrations of a cardio electrogram.
Figure 9B:
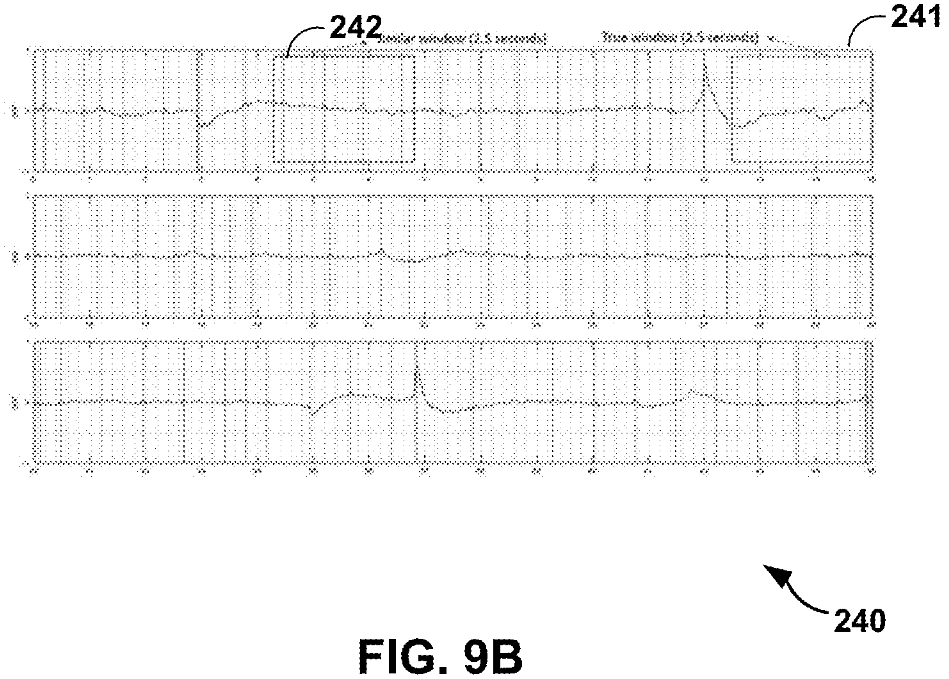

FIGS. 9A-B are both illustrations of cardiac EGMs and illustrate a determination of relative flatness of a potential pause-triggered episode. FIG. 9A illustrates an example EGM 230 and time intervals 231 and 232 for determining the relatively flatness of the true pause. FIG. 9B illustrates an example EGM 240 of a false pause episode and time intervals 241 and 242 for determining the relatively flatness of the false pause.

Time intervals 231 and 232 of FIG. 9A and time intervals 241 and 242 of FIG. 9B are used in one or more false pause-triggered episode detection criterion as described herein for determining the relatively flatness from amplitude values (i.e., at least one amplitude criterion). By applying the at least one amplitude criterion to the amplitude values of example EGMs 230 and 240, the described medical system and technique (e.g., medical system 2) may differentiate example EGM 230, the true pause episode, from example EGM 240, the false pause episode. One example amplitude criterion compares amplitude variation measurements between first time interval 231 and second time interval 232 (or between first time interval 241 and second time interval 242) and when that comparison indicates a considerable amount of amplitude variation, the example amplitude criterion is satisfied. An example of considerable amplitude variation occurs when a max-min amplitude difference of the first time interval 231 is greater than a max-min amplitude difference of the second time interval 232. Another example of considerable amplitude variation occurs when a difference between the max-min amplitude difference of the second time interval 232 and the max-min amplitude difference of the first time interval 231 is less than a threshold difference.

To determine a given pause-triggered episode's relative flatness, two time intervals within that episode are selected. The following description utilizes 2.5 second time because the pause-triggered persisted for 3 seconds; hence, the described medical system and technique is not limited to a specific amount of time but may be set to any suitable amount of time less than a duration of the pause-triggered episode. If the pause-triggered episode lasted for five seconds, the time intervals may be set to 4.5 or 5 seconds. The described medical system and technique also may depend on the pause-triggered episode duration threshold and/or an amount of EGM data stored relative to the pause-triggered episode detection. In general, a candidate window is the time interval between a timepoint 0.5 seconds after the last pre-pause beat and a pause detection timepoint. In FIGS. 9A-B, all of the last pre-pause beats were sensed at the 12 second timepoint (which is illustrated as a mark) and all of the pause detections were sensed at the 15 second timepoint, making the candidate windows between the 12.5 and 15 second timepoints. The described medical system and technique may change this time interval if example EGM 230 and 240 stored additional pre-pause ECG data and/or if the pause-triggered episode duration threshold was set to a length of time other than 3 seconds.

In one example, the first time interval, a candidate window, consists of the EGM between the 12.5 and 15 second marks of the pause-triggered episode when a pause occurred between the 12 and 15 second marks. The first time interval tends to be relatively flat in true pause episodes, while false pause episodes tend to have artifact/noise signal and/or beats that are not detected by the device in this period. A start time for this window is the 12.5 second mark (rather than the 12 second mark) in order to avoid wide QRS complexes or T-waves following the last pre-pause beat at the 12 second mark. For the second time interval, a comparison window of 2.5 second duration is chosen from the pause-triggered episode.

The comparison window of the second time interval must satisfy a number of conditions, such as the following conditions: 1) The comparison window should not overlap with the 12.5-15 second candidate window; 2) The 2.5 second comparison window should not have any noisy or PVC beats; and 3) The comparison window must contain at least two normal beat markers.

The second time interval is determined by starting to search from the first 500 ms of the episode and moving the window until an acceptable 2.5 second window which satisfies all three above-mentioned conditions is obtained. If the 2.5 second window does not satisfy all three conditions, the search window is moved to the next beat marker and the 3 seconds after the marker are analyzed for the three conditions. If the conditions are satisfied, then the comparison window is chosen from the 0.5 second mark of the beat marker till the 3 second mark (for a total of 2.5 seconds).

After finding an acceptable comparison window to use as the second time interval, the following steps are performed to determine that the first time interval indicates a true pause or a false pause: 1) Subtract a mean from a 2.5 second ECG in the comparison window; 2) Find the minimum and maximum amplitude values in the comparison window; 3) Compute the comparison window difference (e.g., maximum amplitude minus minimum amplitude); 4) Repeat steps 1-3 for the candidate window of the first time interval and compute the candidate window difference (e.g., maximum amplitude minus minimum amplitude); and 5) Compute a final difference between comparison window and candidate window (e.g., comparison window difference minus candidate window difference).

For true pause episodes, the comparison window difference is expected to be high and the candidate window difference is expected to be comparatively lower due to the true pause. Thus, we can expect to see large and positive final difference values (e.g., any value between 0 and 20000). Whereas, for false pause episodes, both the candidate window and comparison window difference values are expected to be closer together, and more final difference values are expected to be negative or closer to zero.

A second false pause episode detection criterion corresponding to amplitude values includes a maximum amplitude objective for normal beats in the first time interval. By way of such a maximum amplitude objective, medical system 2 determines how many samples in the candidate window have amplitude values that cross a maximum amplitude limit for the first time interval. If the samples crossing this limit exceed the maximum amplitude objective, a probability for the true false episode decreases.

Computing the maximum amplitude limit may include performing the following steps: 1) Compute, for each normal beat marker in the 45 second cardiac EGM, a maximum amplitude value among one or more (e.g., 20) samples before and after the marker; 2) Compute a median of the maximum amplitudes of all the normal beats; 3) Compute the number of samples in the 2.5 second candidate window (e.g., from the 12.5 to 15 second marks in the episode) where the amplitude crosses the (median—first parameter) value; and 5) compare the number of samples to a second parameter. Medical system 2 classifies the episode as a false pause episode if the number of samples crossing the (median—first parameter) value is greater than the second parameter.

The first and second parameters may be optimized to obtain a desired balance between sensitivity and specificity for the relative flatness of the cardiac EGM. Medical system 2 may calibrate the first and second parameters to achieve different pairs of sensitivity and specificity values for the classification and prioritization of cardiac EGM data for pause-triggered episodes. An example of the first parameter may be a value of 500 and an example of the second parameter may be zero (0), one (1), or two (2).

Figure 10A:
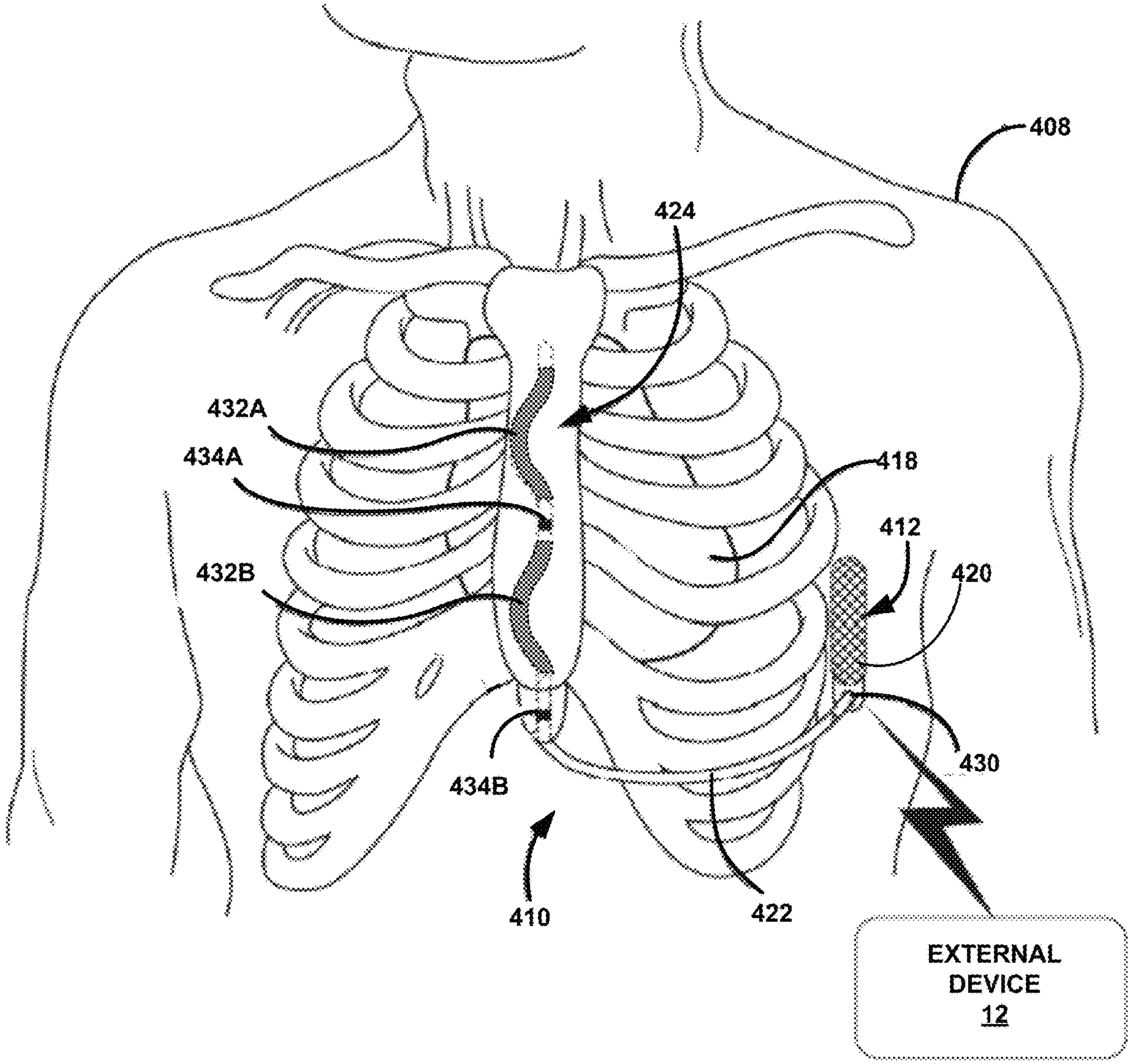
FIG. 10A is a conceptual drawing illustrating a front view of a patient with another example medical system.
Figure 10B:
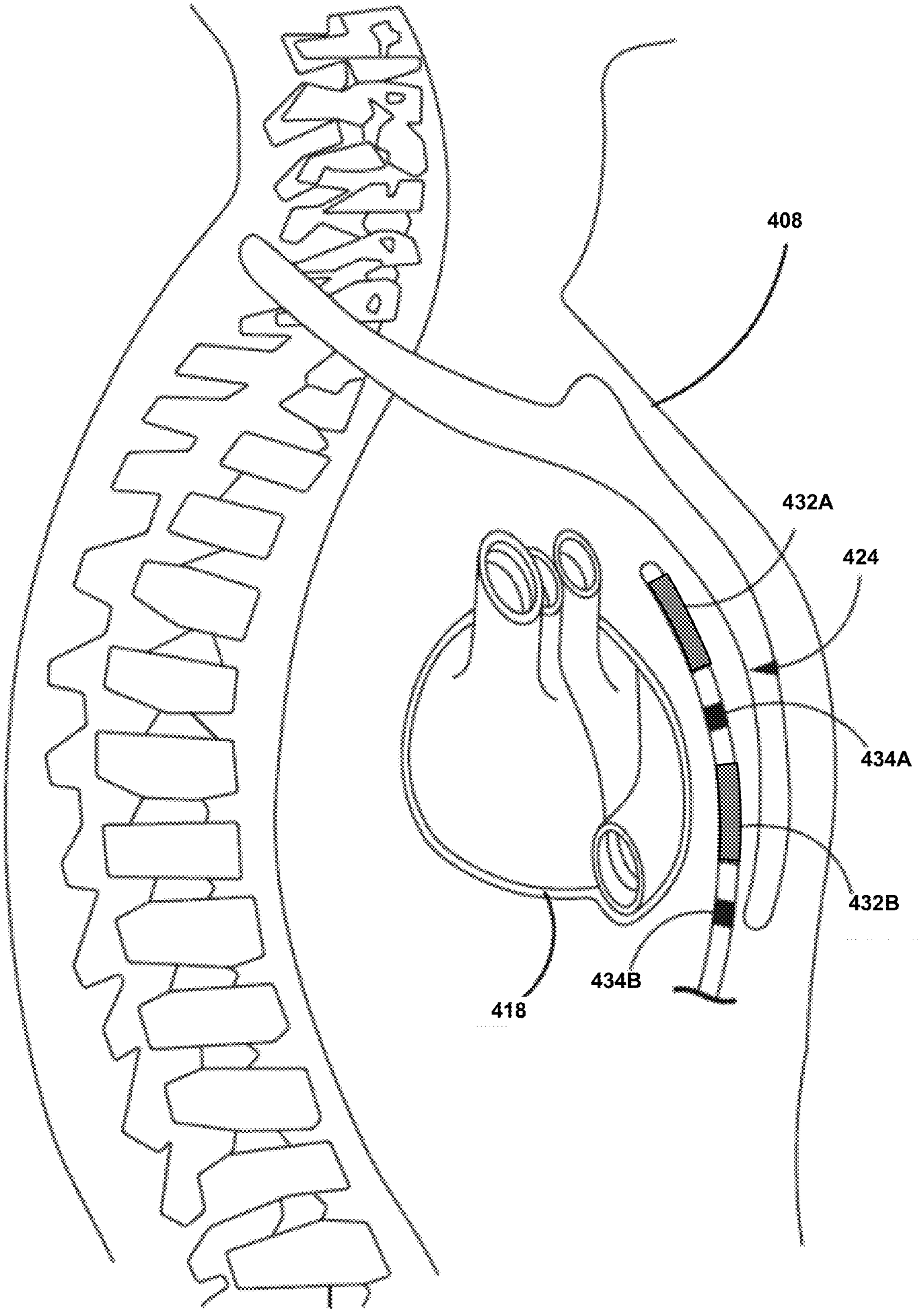
FIG. 10B is a conceptual drawing illustrating a side view of the patient with the example medical system of FIG. 10A.
Figure 10C:
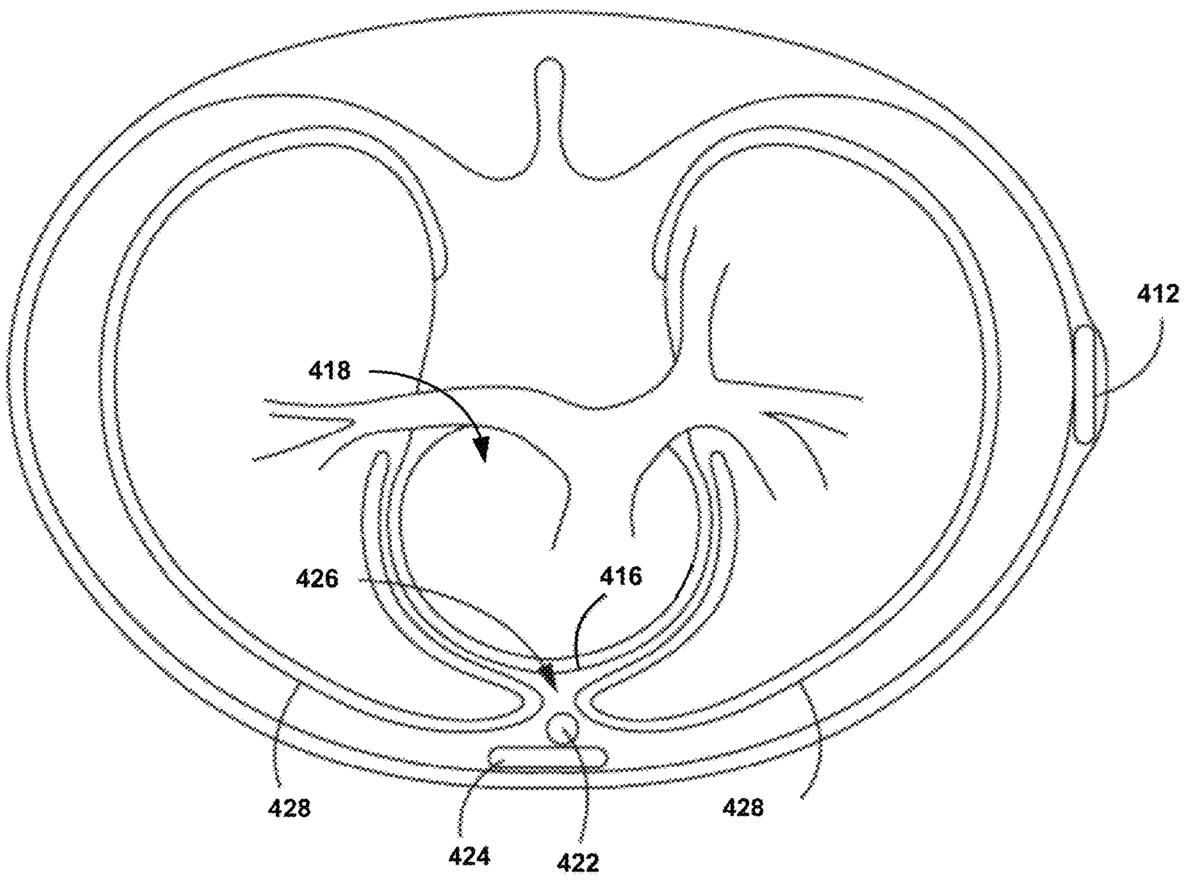
FIG. 10C is a conceptual drawing illustrating a transverse view of the patient with the example medical system of FIG. 10A.

FIGS. 10A-10C are conceptual diagrams of another example medical system 410 implanted within a patient 408. FIG. 10A is a front view of medical system 410 implanted within patient 408. FIG. 10B is a side view of medical system 410 implanted within patient 408. FIG. 10C is a transverse view of medical device system 410 implanted within patient 408.

In some examples, the medical system 410 is an extravascular implantable cardioverter-defibrillator (EV-ICD) system implanted within patient 408. Medical system 410 includes IMD 412, which in the illustrated example is implanted subcutaneously or submuscularly on the left midaxillary of patient 408, such that IMD 412 may be positioned on the left side of patient 408 above the ribcage. In some other examples, IMD 412 may be implanted at other subcutaneous locations on patient 408 such as at a pectoral location or abdominal location. IMD 412 includes housing 420 that may form a hermetic seal that protects components of IMD 412. In some examples, housing 420 of IMD 412 may be formed of a conductive material, such as titanium, or of a combination of conductive and non-conductive materials, which may function as a housing electrode. IMD 412 may also include a connector assembly (also referred to as a connector block or header) that includes electrical feedthroughs through which electrical connections are made between lead 422 and electronic components included within the housing.

IMD 412 may provide the cardiac EGM sensing, asystole detection, and other functionality described herein with respect to IMD 10, and housing 420 may house circuitries 50-62 and an antenna 26 (FIGS. 2 and 3) that provide such functionality. Housing 420 may also house therapy delivery circuitry configured to generate therapeutic electric signals, such as cardiac pacing and anti-tachyarrhythmia shocks, for delivery to patient 408. System 410 may include an external device 12 that may function with IMD 412 as described herein with respect to IMD 10 and system 2.

In the illustrated example, IMD 412 is connected to at least one implantable cardiac lead 422. Lead 422 includes an elongated lead body having a proximal end that includes a connector (not shown) configured to be connected to IMD 412 and a distal portion that includes electrodes 432A, 432B, 434A, and 434B. Lead 422 extends subcutaneously above the ribcage from IMD 412 toward a center of the torso of patient 408. At a location near the center of the torso, lead 422 bends or turns and extends intrathoracically superior under/below sternum 424. Lead 422 thus may be implanted at least partially in a substernal space, such as at a target site between the ribcage or sternum 424 and heart 418. In one such configuration, a proximal portion of lead 422 may be configured to extend subcutaneously from IMD 12 toward sternum 24 and a distal portion of lead 22 may be configured to extend superior under or below sternum 424 in the anterior mediastinum 426 (FIG. 1C).

For example, lead 422 may extend intrathoracically superior under/below sternum 424 within anterior mediastinum 426. Anterior mediastinum 426 may be viewed as being bounded posteriorly by pericardium 416, laterally by pleurae 428, and anteriorly by sternum 424. In some examples, the anterior wall of anterior mediastinum 426 may also be formed by the transversus thoracis and one or more costal cartilages. Anterior mediastinum 426 includes a quantity of loose connective tissue (such as areolar tissue), some lymph vessels, lymph glands, substernal musculature (e.g., transverse thoracic muscle), and small vessels or vessel branches. In one example, the distal portion of lead 422 may be implanted substantially within the loose connective tissue and/or substernal musculature of anterior mediastinum 426. In such examples, the distal portion of lead 422 may be physically isolated from pericardium 416 of heart 418. A lead implanted substantially within anterior mediastinum 426 is an example of a substernal lead or, more generally, an extravascular lead.

The distal portion of lead 422 is described herein as being implanted substantially within anterior mediastinum 426. Thus, some of distal portion of lead 422 may extend out of anterior mediastinum 426 (e.g., a proximal end of the distal portion), although much of the distal portion may be positioned within anterior mediastinum 426. In other embodiments, the distal portion of lead 422 may be implanted intrathoracically in other non-vascular, extra-pericardial locations, including the gap, tissue, or other anatomical features around the perimeter of and adjacent to, but not attached to, the pericardium 416 or other portion of heart 418 and not above sternum 424 or the ribcage. Lead 422 may be implanted anywhere within the "substernal space" defined by the undersurface between the sternum and/or ribcage and the body cavity but not including pericardium 416 or other portions of heart 418. The substernal space may alternatively be referred to by the terms "retrosternal space" or "mediastinum" or "infrasternal" as is known to those skilled in the art and includes the anterior mediastinum 426. The substernal space may also include the anatomical region described in Baudoin, Y. P., et al., entitled "The superior epigastric artery does not pass through Larrey's space (trigonum sternocostale)." Surg. Radiol. Anat. 25.3-4 (2003): 259-62 as Larrey's space. In other words, the distal portion of lead 422 may be implanted in the region around the outer surface of heart 418, but not attached to heart 418. For example, the distal portion of lead 422 may be physically isolated from pericardium 416.

Lead 422 may include an insulative lead body having a proximal end that includes connector 430 configured to be connected to IMD 412 and a distal portion that includes one or more electrodes. As shown in FIG. 10A, the one or more electrodes of lead 422 may include electrodes 432A, 432B, 434A, and 434B, although in other examples, lead 422 may include more or fewer electrodes. Lead 422 also includes one or more conductors that form an electrically conductive path within the lead body and interconnect the electrical connector and respective ones of the electrodes.

Electrodes 432A, 432B may be defibrillation electrodes (individually or collectively "defibrillation electrode(s) 432"). Although electrodes 432 may be referred to herein as "defibrillation electrodes 432," electrodes 432 may be configured to deliver other types of anti-tachyarrhythmia shocks, such as cardioversion shocks. Though defibrillation electrodes 432 are depicted in FIGS. 10A-18C as coil electrodes for purposes of clarity, it is to be understood that defibrillation electrodes 432 may be of other configurations in other examples. Defibrillation electrodes 432 may be located on the distal portion of lead 422, where the distal portion of lead 422 is the portion of lead 422 that is configured to be implanted extravascularly below the sternum 424.

Lead 422 may be implanted at a target site below or along sternum 424 such that a therapy vector is substantially across a ventricle of heart 418. In some examples, a therapy vector (e.g., a shock vector for delivery of anti-tachyarrhythmia shock) may be between defibrillation electrodes 432 and a housing electrode formed by or on IMD 412. The therapy vector may, in one example, be viewed as a line that extends from a point on defibrillation electrodes 432 (e.g., a center of one of the defibrillation electrodes 432) to a point on a housing electrode of IMD 412. As such, it may be advantageous to increase an amount of area across which defibrillation electrodes 432 (and therein the distal portion of lead 422) extends across heart 418. Accordingly, lead 422 may be configured to define a curving distal portion as depicted in FIG. 10A. In some examples, the curving distal portion of lead 22 may help improve the efficacy and/or efficiency of pacing, sensing, and/or defibrillation to heart 418 by IMD 412.

Electrodes 434A, 434B may be pace/sense electrodes (individually or collectively, "pace/sense electrode(s) 434") located on the distal portion of lead 422. Electrodes 434 are referred to herein as pace/sense electrodes as they generally are configured for use in delivery of pacing pulses and/or sensing of cardiac electrical signals. In some instances, electrodes 434 may provide only pacing functionality, only sensing functionality, or both pacing functionality and sensing functionality. In the example illustrated in FIG. 10A and FIG. 10B, pace/sense electrodes 434 are separated from one another by defibrillation electrode 432B. In other examples, however, pace/sense electrodes 434 may be both distal of defibrillation electrode 432B or both proximal of defibrillation electrode 432B. In examples in which lead 422 includes more or fewer electrodes 432, 434, such electrodes may be positioned at other locations on lead 422.

In the example of FIG. 10A, the distal portion of lead 422 is a serpentine shape that includes two "C" shaped curves, which together may resemble the Greek letter epsilon, "ε." Defibrillation electrodes 432 are each carried by one of the two respective C-shaped portions of the lead body distal portion. The two C-shaped curves extend or curve in the same direction away from a central axis of the lead body. In some examples, pace/sense electrodes 434 may be approximately aligned with the central axis of the straight, proximal portion of lead 422. In such examples, mid-points of defibrillation electrodes 432 are laterally offset from pace/sense electrodes 434. Other examples of extra-cardiovascular leads including one or more defibrillation electrodes and one or more pace/sense electrodes 434 carried by curving, serpentine, undulating or zig-zagging distal portion of lead 422 also may be implemented using the techniques described herein. In some examples, the distal portion of lead 422 may be straight (e.g., straight or nearly straight).

Deploying lead 422 such that electrodes 432, 434 are at the depicted peaks and valleys of serpentine shape may provide access to preferred sensing or therapy vectors. Orienting the serpentine shaped lead such that pace/sense electrodes 434 are closer to heart 418 may provide better electrical sensing of the cardiac signal and/or lower pacing capture thresholds than if pace/sense electrodes 434 were oriented further from heart 418. The serpentine or other shape of the distal portion of lead 422 may have increased fixation to patient 408 as a result of the shape providing resistance against adjacent tissue when an axial force is applied. Another advantage of a shaped distal portion is that electrodes 432, 434 may have access to greater surface area over a shorter length of heart 418 relative to a lead having a straighter distal portion.

In some examples, the elongated lead body of lead 422 may include one or more elongated electrical conductors (not illustrated) that extend within the lead body from the connector at the proximal lead end to electrodes 432, 434 located along the distal portion of lead 422. The one or more elongated electrical conductors contained within the lead body of lead 422 may engage with respective ones of electrodes 432, 434. The conductors may electrically couple to circuitry, such as a therapy delivery circuitry and sensing circuitry 52, of IMD 412 via connections in connector assembly. The electrical conductors transmit therapy from the therapy delivery circuitry to one or more of electrodes 432, 434, and transmit sensed cardiac EGMs from one or more of electrodes 432, 434 to sensing circuitry 52 within IMD 412.

In general, IMD 412 may sense cardiac EGMs, such as via one or more sensing vectors that include combinations of pace/sense electrodes 434 and/or a housing electrode of IMD 412. In some examples, IMD 412 may sense cardiac EGMs using a sensing vector that includes one or both of the defibrillation electrodes 432 and/or one of defibrillation electrodes 432 and one of pace/sense electrodes 434 or a housing electrode of IMD 412. Medical system 410, including processing circuitry of IMD 412 and/or external device 12, may perform any of the techniques described herein for determining whether asystole detection and false asystole detection criteria are satisfied, e.g., based on cardiac EGMs sensed via extravascular electrodes 432, 434. Cardiac EGMs sensed via extravascular electrodes may include noise, e.g., due to changing contact with tissue and/or orientation relative to heart, in a similar manner as described herein with respect to subcutaneous electrodes. In general, when electrodes are not fixed directly to the myocardium, motion, e.g., respiratory motion, can cause variability in depolarization amplitudes and other noise that may lead to false asystole detections. The techniques described herein may be implemented with cardiac EGMs sensed via subcutaneous electrodes, cutaneous electrodes, substernal electrodes, extravascular electrodes, intra-muscular electrodes, or any electrodes positioned in (or in contact with) any tissue of a patient.

The techniques described in this disclosure may be implemented, at least in part, in hardware, software, firmware, or any combination thereof. For example, various aspects of the techniques may be implemented within one or more microprocessors, DSPs, ASICs, FPGAs, or any other equivalent integrated or discrete logic QRS circuitry, as well as any combinations of such components, embodied in external devices, such as physician or patient programmers, stimulators, or other devices. The terms "processor" and "processing circuitry" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as RAM, DRAM, SRAM, magnetic discs, optical discs, flash memories, or forms of EPROM or EEPROM. The instructions may be executed to support one or more aspects of the functionality described in this disclosure.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

What is claimed is:

1. A cardiac stimulation device comprising:

sensing circuitry configured to sense cardiac electrograms via a plurality of electrodes;

therapy delivery circuitry;

a storage medium; and processing circuitry configured to:

control the sensing circuitry to sense a cardiac electrogram of a pause-triggered episode;

control the storage medium to store data corresponding to the cardiac electrogram of the pause-triggered episode;

determine whether one or more of false pause detection criteria are satisfied based on the cardiac electrogram, wherein the one or more of false pause detection criteria comprise:

at least one criterion for relative flatness of amplitude values of the cardiac electrogram in a time interval between a last pre-pause beat and a pause detection timepoint;

classify the pause-triggered episode as one of a plurality of classifications based on the determination of whether the one or more false pause detection criteria are satisfied; and control the therapy delivery circuitry to provide cardiac stimulation therapy to a patient based on the classification indicating that the pause-triggered episode is a true pause, wherein the at least one criterion comprises a criterion that is satisfied based upon determining that a maximum-minimum amplitude difference in the time interval is greater than or equal to a maximum-minimum amplitude difference in another time interval.

2. The cardiac stimulation device of claim 1, wherein the processing circuitry is configured to:

classify the pause-triggered episode as a likely true pause episode with high priority based upon the determination that none of the false pause detection criteria are satisfied.

3. The cardiac stimulation device of claim 2, wherein the processing circuitry is further configured to:

determine whether at least one additional false pause detection criterion is satisfied based on the cardiac electrogram; and classify the pause-triggered episode as a likely false pause episode with low priority based upon a determination that at least one additional false pause detection criterion is satisfied.

4. The cardiac stimulation device of claim 3, wherein the processing circuitry is further configured to classify the pause-triggered episode as a likely false pause-triggered episode with normal priority based upon a determination that none of the at least one additional false pause detection criterion are satisfied.

5. The cardiac stimulation device of claim 1, wherein each of the plurality of classifications comprises a respective priority indicium.

6. The cardiac stimulation device of claim 5, wherein the processing circuitry is further configured to insert the cardiac electrogram into one of a plurality of review queues for a review process based on the priority indicium.

7. The cardiac stimulation device of claim 1, wherein the plurality of classifications comprise a true pause and a false pause.

8. The cardiac stimulation device of claim 1, wherein the one or more of false pause detection criteria comprise a criterion including a threshold number of normal beats for the cardiac electrogram.

9. The cardiac stimulation device of claim 1, wherein the one or more false pause detection criteria comprise a criterion that is satisfied based upon a determination that a number of normal beats in the cardiac electrogram is less than a normal beat threshold.

10. The cardiac stimulation device of claim 1, wherein the one or more of false pause detection criteria comprise a criterion that is based on a noise status of the last pre-pause beat in the cardiac electrogram.

11. The cardiac stimulation device of claim 1, wherein the one or more of false pause detection criteria comprise a criterion that is satisfied based upon identifying in the cardiac electrogram that the last pre-pause beat is noisy.

12. The cardiac stimulation device of claim 1, wherein the at least one criterion comprises a criterion that is satisfied based upon not determining that the amplitude values in the time interval are relatively flat compared to another time interval.

13. The cardiac stimulation device of claim 1, wherein the one or more false pause detection criteria comprise a criterion that is satisfied based upon determining that, in the time interval, a number of samples crossing a first parameter is greater than a second parameter, wherein the first parameter includes a maximum amplitude limit and the second parameter includes a threshold number of samples crossing the maximum amplitude limit.

14. The cardiac stimulation device of claim 1, wherein the processing circuitry is further configured to identify noise or an artifact in a signal for the cardiac electrogram based upon the relative flatness of the amplitudes in the time interval.

15. The cardiac stimulation device of claim 1, wherein the cardiac stimulation device is an implantable cardioverter-defibrillator.

16. A method comprising:

sensing, by sensing circuitry of a system, a cardiac electrogram of a pause-triggered episode via a plurality of electrodes of the system;

determining, by processing circuitry of the system, whether one or more of false pause detection criteria are satisfied based on the cardiac electrogram, wherein the one or more of false pause detection criteria comprise:

at least one criterion for relative flatness of amplitude values of the cardiac electrogram in a time interval between a last pre-pause beat and a pause detection timepoint;

classifying, by the processing circuitry, the pause-triggered episode as one of a plurality of classifications based on the determination of whether the one or more false pause detection criteria are satisfied; and controlling therapy delivery circuitry of the system to provide cardiac stimulation therapy to a patient based on the classification indicating that the pause-triggered episode is a true pause, wherein the at least one criterion for relative flatness comprises a criterion that is satisfied based upon determining that a maximum-minimum amplitude difference in the time interval is greater than or equal to a maximum-minimum amplitude difference in another time interval.

17. The method of claim 16, wherein determining whether the one or more of false pause detection criteria are satisfied further comprises determining whether at least one amplitude criterion is satisfied based upon determining that the amplitude values in the time interval are not relatively flat compared to another time interval.

18. The method of claim 16, wherein determining whether the one or more of false pause detection criteria are satisfied further comprises determining whether at least one amplitude criterion is satisfied based upon determining that, in the time interval, a number of samples crossing a first parameter is greater than a second parameter, wherein the first parameter includes a limit on maximum amplitude value and the second parameter includes a number of samples crossing the limit on maximum amplitude value.

19. A non-transitory computer-readable storage medium comprising program instructions that, when executed by processing circuitry of a medical system, cause the processing circuitry to:

control sensing circuitry of the medical system to sense a cardiac electrogram of a pause-triggered episode, the cardiac electrogram sensed via a plurality of electrodes;

determine whether one or more of false pause detection criteria are satisfied based on the cardiac electrogram, wherein the one or more of false pause detection criteria comprise:

at least one criterion for relative flatness of amplitude values of the cardiac electrogram in a time interval between a last pre-pause beat and a pause detection timepoint;

classify the pause-triggered episode as one of a plurality of classifications based on the determination of whether the one or more false pause detection criteria are satisfied; and control a cardiac stimulation device therapy delivery circuitry of the medical system to provide cardiac stimulation therapy to a patient based on the classification indicating that the pause-triggered episode is a true pause, wherein the at least one criterion for relative flatness comprises a criterion that is satisfied based upon determining that a maximum-minimum amplitude difference in the time interval is greater than or equal to a maximum-minimum amplitude difference in another time interval.

* * * * *